US011957923B2

(12) United States Patent
Forsell

(10) Patent No.: US 11,957,923 B2
(45) Date of Patent: *Apr. 16, 2024

(54) SYSTEM FOR VOICE CONTROL OF A MEDICAL IMPLANT

(71) Applicant: Peter Forsell, Lund (SE)

(72) Inventor: Peter Forsell, Lund (SE)

( * ) Notice: Subject to any disclaimer, the term of this patent is extended or adjusted under 35 U.S.C. 154(b) by 450 days.

This patent is subject to a terminal disclaimer.

(21) Appl. No.: 17/223,104

(22) Filed: Apr. 6, 2021

(65) Prior Publication Data
US 2021/0220653 A1 Jul. 22, 2021

Related U.S. Application Data

(63) Continuation of application No. 14/948,434, filed on Nov. 23, 2015, now Pat. No. 11,000,687, which is a
(Continued)

(51) Int. Cl.
| | | |
|---|---|---|
| *G10L 15/20* | (2006.01) | |
| *A61M 5/142* | (2006.01) | |
| *A61N 1/00* | (2006.01) | |
| *A61N 1/372* | (2006.01) | |
| *A61N 1/378* | (2006.01) | |
| *A61F 2/00* | (2006.01) | |
| *A61F 2/01* | (2006.01) | |
| *A61F 2/04* | (2013.01) | |
| *A61F 2/24* | (2006.01) | |

(Continued)

(52) U.S. Cl.
CPC ........... *A61N 1/3787* (2013.01); *A61M 5/142* (2013.01); *A61N 1/00* (2013.01); *A61N 1/37211* (2013.01); *A61N 1/37217* (2013.01); *A61F 2/0036* (2013.01); *A61F 2/01* (2013.01); *A61F 2002/044* (2013.01); *A61F 2/24* (2013.01); *A61F 2250/0001* (2013.01); *A61M 5/14* (2013.01); *A61M 2205/80* (2013.01); *G10L 15/20* (2013.01); *G10L 2015/223* (2013.01); *G10L 15/26* (2013.01); *G10L 21/02* (2013.01); *G10L 21/0208* (2013.01); *G10L 2021/02165* (2013.01); *G10L 25/84* (2013.01)

(58) Field of Classification Search
None
See application file for complete search history.

(56) References Cited

U.S. PATENT DOCUMENTS 5,267,323 A * 11/1993 Kimura .................... H04B 1/48
704/E15.045
2001/0032085 A1* 10/2001 Goedeke ............ A61N 1/37247
704/E15.044
(Continued)

*Primary Examiner* — Jakieda R Jackson

(57) ABSTRACT

A system for communicating with a medical implant in a body of a user is provided. The system comprises a command generator and a memory, wherein the command generator is configured to receive a voice command from the user and to reduce noise, generated by the body, from the received voice command to generate a noise-reduced voice command. The command generator is further configured to compare the noise-reduced voice command with previously stored voice commands and to transmit a command signal to the implant in case the noise-reduced voice command corresponds to any of the previously received commands stored in the memory.

20 Claims, 20 Drawing Sheets

Related U.S. Application Data continuation of application No. 13/384,377, filed as application No. PCT/SE2010/050858 on Jul. 19, 2010, now Pat. No. 9,192,773.

(60) Provisional application No. 61/213,806, filed on Jul. 17, 2009.

(51) Int. Cl.
| | |
|---|---|
| A61M 5/14 | (2006.01) |
| G10L 15/22 | (2006.01) |
| G10L 15/26 | (2006.01) |
| G10L 21/02 | (2013.01) |
| G10L 21/0208 | (2013.01) |
| G10L 21/0216 | (2013.01) |
| G10L 25/84 | (2013.01) |

(56) References Cited

U.S. PATENT DOCUMENTS

| | | | |
|---|---|---|---|
| 2002/0026122 A1* | 2/2002 | Lee | A61B 5/0031 600/523 |
| 2002/0099412 A1* | 7/2002 | Fischell | A61N 1/36135 607/3 |
| 2002/0186852 A1* | 12/2002 | Rademacher | G10L 21/0208 381/94.1 |
| 2002/0191804 A1* | 12/2002 | Luo | H04R 5/04 381/317 |
| 2002/0193847 A1* | 12/2002 | Daum | A61N 1/3625 607/60 |
| 2004/0059573 A1* | 3/2004 | Cheong | G10L 15/20 704/E21.012 |
| 2004/0064133 A1* | 4/2004 | Miller | A61B 5/14552 604/890.1 |
| 2004/0083107 A1* | 4/2004 | Noda | G10L 15/22 704/E15.04 |
| 2004/0117825 A1* | 6/2004 | Watkins | H04N 21/4334 348/E5.002 |
| 2004/0165736 A1* | 8/2004 | Hetherington | G10L 21/0208 381/94.1 |
| 2004/0213419 A1* | 10/2004 | Varma | H04R 3/005 381/71.11 |
| 2005/0047611 A1* | 3/2005 | Mao | H04R 3/005 381/92 |
| 2005/0240236 A1* | 10/2005 | Daum | A61N 1/37217 607/27 |
| 2005/0245839 A1* | 11/2005 | Stivoric | A61B 5/0008 374/E1.004 |
| 2006/0087924 A1* | 4/2006 | Fried | H04B 1/385 369/30.01 |
| 2006/0136744 A1* | 6/2006 | Lange | G06V 40/10 713/186 |
| 2007/0049363 A1* | 3/2007 | Green | G05B 19/042 455/575.2 |
| 2007/0198255 A1* | 8/2007 | Fingscheidt | G10L 21/0208 704/228 |
| 2008/0091434 A1* | 4/2008 | Rodriguez | H04N 21/42203 704/275 |
| 2008/0159573 A1* | 7/2008 | Dressler | H04R 25/505 381/317 |
| 2009/0046868 A1* | 2/2009 | Engle | G10K 11/17857 381/74 |
| 2009/0076664 A1* | 3/2009 | McCabe | B60L 3/02 701/2 |
| 2009/0228073 A1* | 9/2009 | Scholten | A61B 5/0031 607/60 |
| 2009/0248411 A1* | 10/2009 | Konchitsky | G10L 21/0208 704/E15.001 |
| 2010/0088093 A1* | 4/2010 | Lee | G10L 15/20 704/E15.045 |
| 2013/0072770 A1* | 3/2013 | Rao | A61N 1/37217 600/323 |
| 2013/0238044 A1* | 9/2013 | Penner | A61N 7/00 607/11 |

\* cited by examiner

SYSTEM FOR VOICE CONTROL OF A MEDICAL IMPLANT

This application is a continuation of U.S. application Ser. No. 14/948,434 filed 23 Nov. 2015, which is a continuation of U.S. application Ser. No. 13/384,377 filed 17 Jan. 2012 and granted as U.S. Pat. No. 9,192,773, which is the National Stage Entry of PCT/SE2010/050858 filed 19 Jul. 2010, which claims the benefit of U.S. Provisional Application No. 61/213,806 filed 17 Jul. 2009, each of which is incorporated herein by reference.

TECHNICAL FIELD

The present invention discloses a system for voice control of and communication with a medical implant for implantation in a mammal body.

BACKGROUND

Medical implants as such are previously known, and are often used to replace or assist an organ or a function in a mammal body. Some medical implants which may be mentioned by way of example are artificial hip joints, pacemakers, artificial insulin pumps and the like.

As will be understood, some medical implants require, or may be improved by, the ability to receive input, either from the patient or medical personnel attending to the patient. Various methods are known for giving such input to implanted devices. For example, U.S. Pat. No. 5,569,186, discloses a system for sending input to an implant via telemetry. In the '186 patent, input can be given as voice commands; if a voice command is successfully recognized by the apparatus, a matching command is then sent by telemetry means to an implantable device in a patient's body.

SUMMARY

It is an object of the present invention to further improve on the ability of a medical implant to receive input commands as voice commands.

This object is addressed by the present invention in that it discloses a system for implantation in a mammal body for the control of and communication with a medical implant in the mammal body; the system of the invention comprises a command input device and a processing device coupled to the command input device.

The processing device of the system is adapted to generate input to a command generator which is also comprised in the system and which is coupled to the processing device and adapted to generate and communicate commands to the medical implant in response to input received from the processing device.

Furthermore, the system of the invention also comprises a memory unit connected to at least one of said devices in the system for storing a memory bank of commands.

The inventive system exhibits the following features:
  it is adapted to be implanted in proximity to the medical implant,
  the command input device is adapted to receive commands from a user as voice commands,
  the commands stored in the memory unit include voice commands,
  the processing device comprises a filter for filtering input received via the command input device,
  the filter is adapted to filter received voice commands against the background of high frequency losses and frequency distortion caused by the mammal body,
  the processing device is adapted to deliver filtered voice commands as input to the command generator which is adapted to compare received voice commands to voice commands stored in the memory unit, and if that comparison yields a likeness, to generate a corresponding command and communicate it to the medical implant.

Thus, by means of the invention, a user can control an implant in a mammal body by means of voice commands, i.e. spoken commands, which naturally will enhance the ease of handing for the user.

The inventor of the present invention has realized that a mammal body such as the human body causes losses, in particular high frequency losses and c frequency distortion to acoustic signals such as voice commands which are generated outside of the body. Both of these factors are taken into account by the filter of the present invention, i.e. the losses and the distortion to outside sounds caused by the body, as has emerged from the description given above.

In one embodiment the filter is adapted to filter received voice commands against the background of high frequency losses and frequency distortion caused by the mammal body based on the specific position of said command input device inside the body.

The filter may have different frequency compensation curves to compensate for the resulting voice command after passing through the mammal body based on the specific position of said command input device inside the body.

The filter may also have different time delay compensations to compensate for the resulting voice command after passing through the mammal body based on the specific position of said command input device inside the body.

In addition, noises caused by the body as such may also interfere with the command input device's reception of voice commands, so in one embodiment of the present invention, the processing device is also adapted to cancel noise which is caused by the mammal body and received by the command input device, in order to reduce or entirely eliminate the amount of such noise comprised in the input to the command generator.

In one embodiment of the inventive system, the processing device is adapted to recognize one more specific noise sources in the mammal body, and to activate the cancellation when noise from such a noise source is detected.

In one embodiment, the cancellation is only activated when the processing device receives a voice input command from a user.

In particular, the internal "noise sources" which the system is adapted to cancel noise from comprise one or more of the following:
  the intestines,
  the respiratory system,
  the heart.

As an alternative to direct cancellation, the processing device takes into account the specific internal sounds such as, for example, heartbeats or respiratory sounds in order to be able to process voice commands. The noise cancellation in such an embodiment means an active processing to counteract the effect of such internally generated sounds.

The voice commands which are stored in the memory of the system of the invention can either be preset by a manufacturer, as an alternative to which they can be "learned" by the system prior to implantation. In the latter case, the commands can be learned on a separate learning device, and then stored in the system's memory. As an alternative to a separate learning device, in one embodiment of the invention, the command generator comprises a learning function which is adapted to perform learning sessions for learning which of a number of voice commands that should be interpreted as meaning one of a number of pre-programmed commands stored in the memory.

In other words, a user utters a certain command a number of times until the system recognizes the command, and the recognized command is then associated with a control command which should be output to the implant when the recognized command is received by the system.

In one embodiment, the system of the invention additionally comprises a wireless receiver for receiving commands from a remote control outside of the mammal body. The commands comprise commands which should also be generated by the command generator upon recognizing a voice command from a user, so that a voice command issued by a user can be accompanied by a wireless command from the remote control during a learning session, in order for the learning function to learn which command that should be generated upon the reception of a certain voice command.

In one embodiment, the system also comprises a wireless transmitter, which the learning function is adapted to use in order to signal to a user during a learning session that a voice command has been learnt by the learning function.

As has been mentioned, the system of the invention is intended for implantation in a mammal body, and is in one embodiment particularly suitable for implantation in the abdomen, thorax or the pelvic region of the mammal body, since, for example, different sound spectra generated by the body and different sound distortion and frequency losses generate specific patterns for each of these locations.

In one embodiment, the command generator and/or the processing device comprises means for receiving signals from the medical implant and for transmitting said signals to a user. In one version of this embodiment, the system uses the transmitter of the learning function for transmitting the received signals from the medical implant wirelessly to the user. The transmitter can be a radio transmitter or a sonic transmitter.

The implant which is controlled by means of the present invention can be of various kinds, all of which are within the scope of the present invention, but examples of which mention may be made include the following:

A controllable engine,
A pump,
A stimulation device,
A constriction device,
A fluid moving device,
A heart pump,
A heart valve,
A filtering device,
A pharmaceutical drug delivery device,
An artificial reservoir,
A fertility or non-fertility device,
A no-reflux device,
A potency treatment device,
A urine incontinence or urine retention device,
An intestinal device,
An aneurysm treatment device,
A hypertension treatment device,
A clot removing device

BRIEF DESCRIPTION OF THE DRAWINGS

The invention will be described in more detail in the following, with reference to the appended drawings, in which.

DETAILED DESCRIPTION

Figure 1:
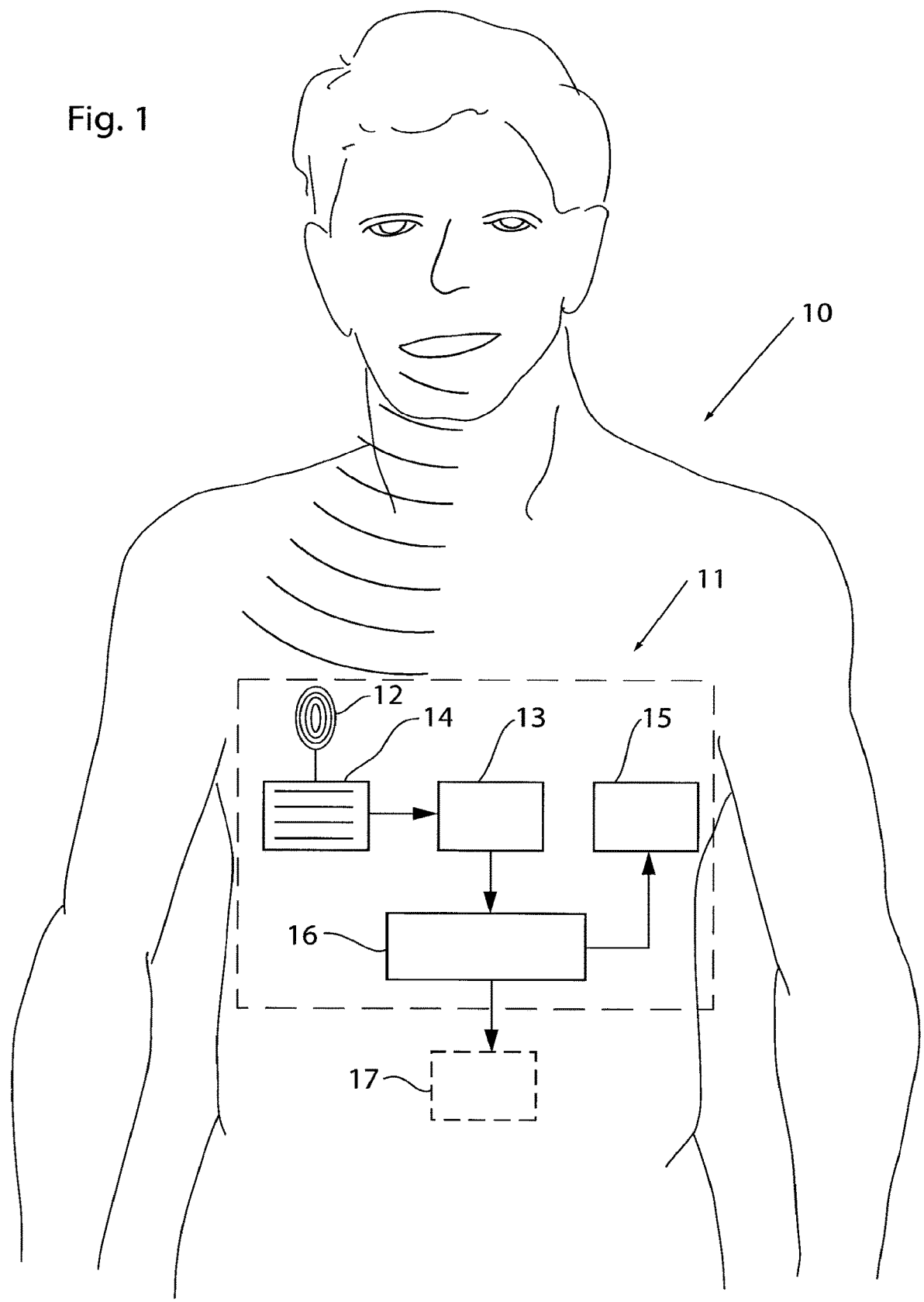
FIG. 1 shows an overview of one embodiment of a system of the invention.

FIG. 1 shows an overview of a system 11 of the invention. The system 11 is shown as being implanted in a mammal body, in this case a human body 10, and as can be seen, the system 11 is electrically connected to a medical implant 17 in the body 10.

The system 10 is intended to control the medical implant 17, and is adapted to be implanted so close to the medical implant 17 that the electrical connection, shows as 18 in FIG. 1, can be a wire-bound connection, although wireless connections are also fully within the scope of the present invention.

The system 11 and its components will be described in more detail in the following, but first an overview of the system's components in the embodiment shown in FIG. 1 will be given. The function of the components of the system 11 will also be explained in more detail following the overview.

The system 11 comprises a command input device 12; since the system 11 is intended to be able to receive commands in the form of spoken commands, the command input device suitably one or more microphones; in the case of more than one microphone, the microphones can be arranged as a so called microphone array. The system 11 also comprises a processing device 13, for example in the form of a microprocessor, and connected to, or incorporated in the processing device 13 there is a filter 14. It should be pointed out that the placement of the filter 14 can be varied within the scope of the invention; for example, the filter 14 can also be placed immediately following the command input device 12, i.e. between the command input device and the processing device 13. As mentioned, the filter 14 can either be comprised in the processing device 13 as such, or it can be separate system component in the system 11.

In addition, the system 11 as such can be an analogue system, i.e. one which uses analogue signals and analogue components, or, alternatively, in a preferred embodiment, the system is based on digital components, and therefore comprises an analogue to digital converter, an ADC, which can be placed for example, immediately following the command input device 12. The ADC can also be a subfunction in the processing device 13. The fact that the system 11 of the invention can be either analogue or digital is true for all of the embodiments described below; the same goes for the reasoning regarding the placement of the ADC.

The system 11 also comprises a command generator 16 and a memory 15, with the memory being coupled to the command generator 16 and/or to the processing device 16.

One function of the command generator 16 is to receive voice commands which have been received from a user via the command input device 12, filtered by the filter 14 and possibly also processed by the processor 13, and to then compare these voice commands with a set of "allowed" voice commands stored in the memory 15; if the comparison yields a positive result, i.e. a received command matches one of the stored commands, the command generator will then output a corresponding command on the connection 18 to the implant 17 for controlling the implant 17.

The notion of "corresponding command" which is output to the implant 17 is needed if the implant can only receive commands as non-spoken commands. Naturally, if the implant 17 as such can accept spoken commands, the system 11 can be adapted so that the command generator 16 can output the commands to the implant 17 as spoken commands.

In one embodiment, the command generator 16 has an output stage which comprises a conductor connected to the medical implant in order to transport commands to the implantable device in response to input received from the processing device 13.

More details on how the system 11 of the invention is adapted to receive spoken commands will be given later in this text. However, first, the function of the filter 14 will be described in more detail.

Since the system 11 of the invention, including the command input device 12, is intended to be implanted inside a mammal body, the inventor of the present invention has realized that the mammal body will have a transfer function on audio signals, e.g. voice commands, which are generated outside the body before they reach the command input device 12. This transfer function needs to be counteracted in order to ensure good function of the system 11. To this end, measurements have been made inside a mammal body, in this case a human body, in order to find the transfer function of the human body.

Figure 2:
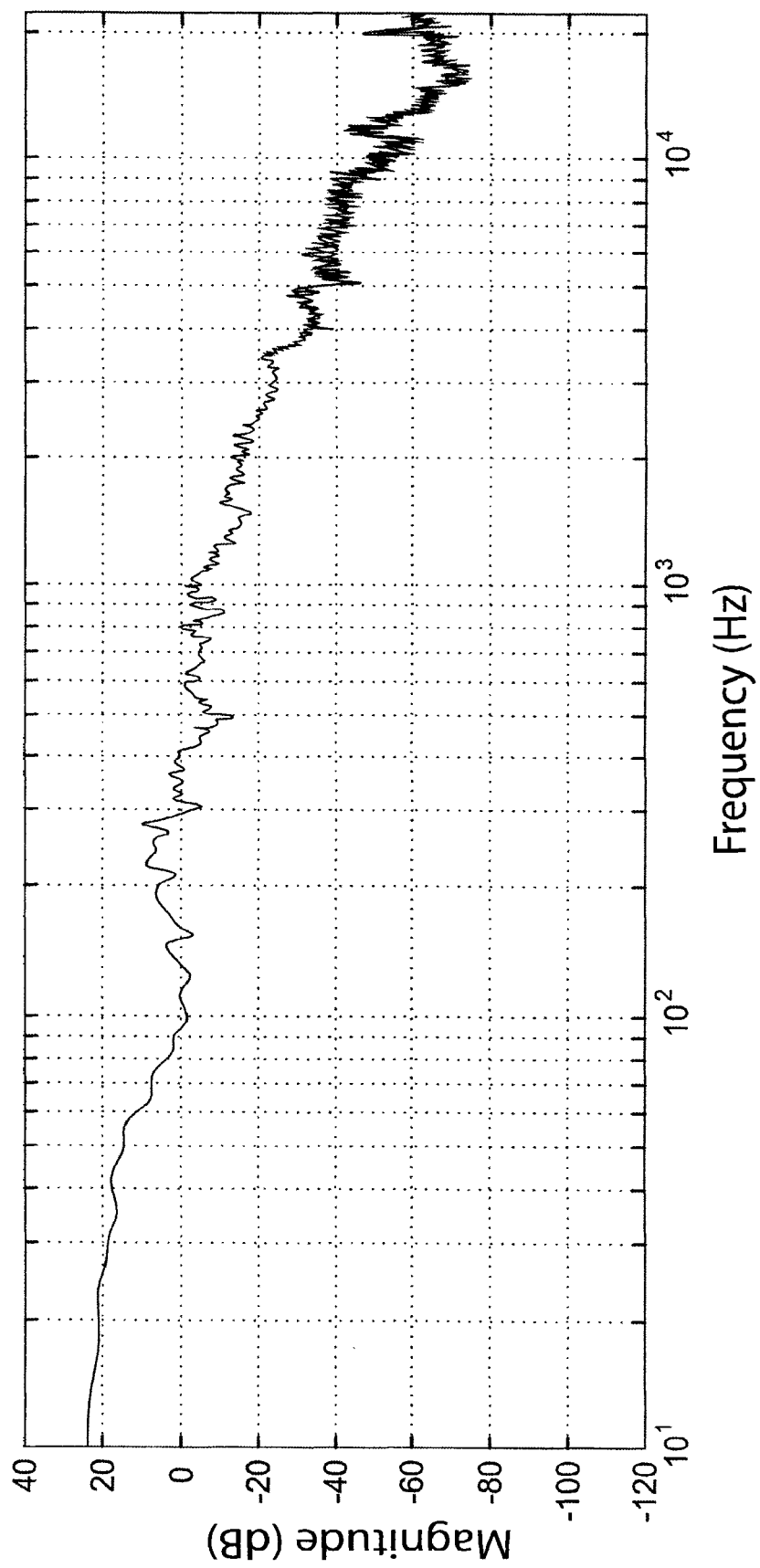
FIG. 2 shows a measured transfer function curve.

FIG. 2 shows a typical transfer function for sound generated outside of a human body as detected by a microphone inside the abdomen. As can be seen, the transfer function exhibits a strong "roll off" in the frequency range above 1 kHz, and an amplification of the frequency range below 100 Hz.

Thus, the filter 14 should be such that it can counteract the transfer function of FIG. 2. Naturally though, the transfer function shown in FIG. 2 and the position in the body where it was measured, i.e. the abdomen, are only examples, as is the human body; the same principles are applicable to other mammal bodies as well. In other embodiments of the invention, the transfer function of more than one position in the body can be measured, and the filter 14 can be programmed or otherwise designed to counteract a transfer function which is specific for a position in the body for which the system 11 is intended, or the filter 14 can be programmed with a number of filter characteristics, one of which can be activated, depending on which position in the body that the system 11 is intended to placed in.

As a further alternative, the filter 14 and/or the processing device 13 can be programmed to detect which of a number of pre-programmed filter functions that best fit the actual transfer function in the position that the system 11 is placed in, so that that system 11 can be "adaptive" in that it chooses one of a number of pre-programmed filter functions that is best suited to the placement of the system 11 after the system is actually implanted in the mammal body 10.

The filter 14 can, as has been mentioned, and as will be realized by those skilled in the field, be designed in a variety of ways, but in one embodiment, the filter 14 is implemented as a digital filter using algorithms for digital signal processing.

In one embodiment the filter 14 is adapted to filter received voice commands against the background of high frequency losses and frequency distortion caused by the mammal body 10 based on the specific position of said command input device 12 inside the body.

The filter 14 may have different frequency compensation curves to compensate for the resulting voice command after passing through the mammal body 10 based on the specific position of said command input device 12 inside the body.

The filter 14 may also have different time delay compensations to compensate for the resulting voice command after passing through the mammal body 10 based on the specific position of said command input device 12 inside the body.

Since the system 11 is adapted to be implanted inside a mammal body, the command input device and conceivably also other parts of the system, may be enclosed in a watertight casing, which will also cause some distortion and loss on audio signals. To compensate for this, in one embodiment, the filter 14 is also adapted to compensate for losses and distortions caused by such a casing.

Apart from the effects of the mammal body on the voice commands generated outside of the mammal body as the commands propagate through the body 10 to the input device 12, in some embodiments of the system 10, the system is also adapted to counteract noises generated within the body, by the body itself, sounds which may interfere with the function of the input device 12 if they are not addressed properly. To this end, the inventor of the present invention has made measurements inside a human body (as an example of a mammal body), in order to ascertain if there are indeed such noises generated inside a mammal body and what their exact nature is, in order to see how they may be best counteracted.

Although noises inside of a mammal body such as the human body may be caused by a large number of organs, some main sources of internal noise have been found to be:
 the intestines,
 the respiratory system,
 the heart's beating.

The inventor of the present invention has performed measurements inside a human body, as an example of a mammal body, in order to ascertain the nature of these noises, in order to determine how best to counteract these noises.

Figure 3:
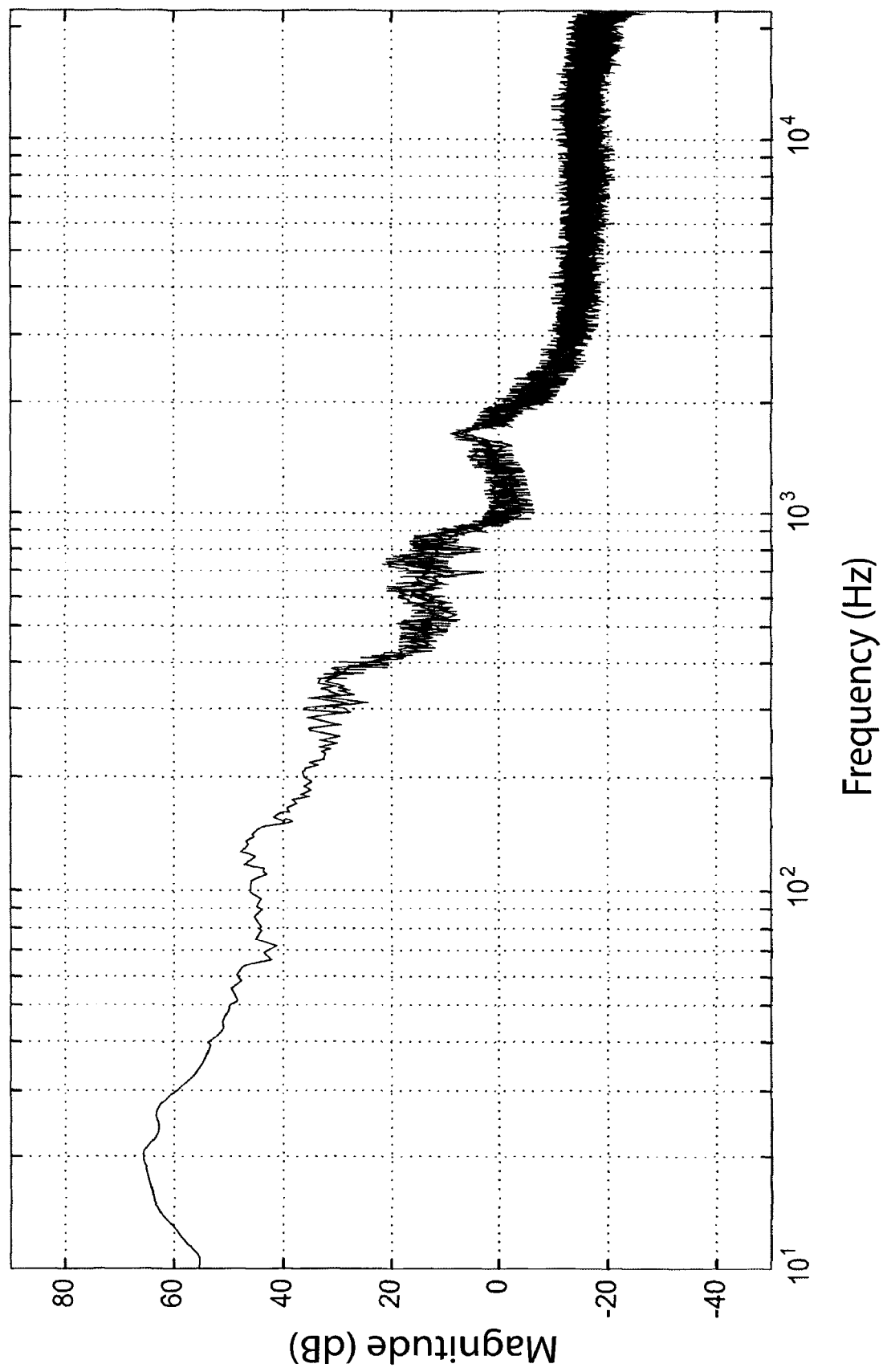
FIGS. 3-5 show measured noise curves.
Figure 4:
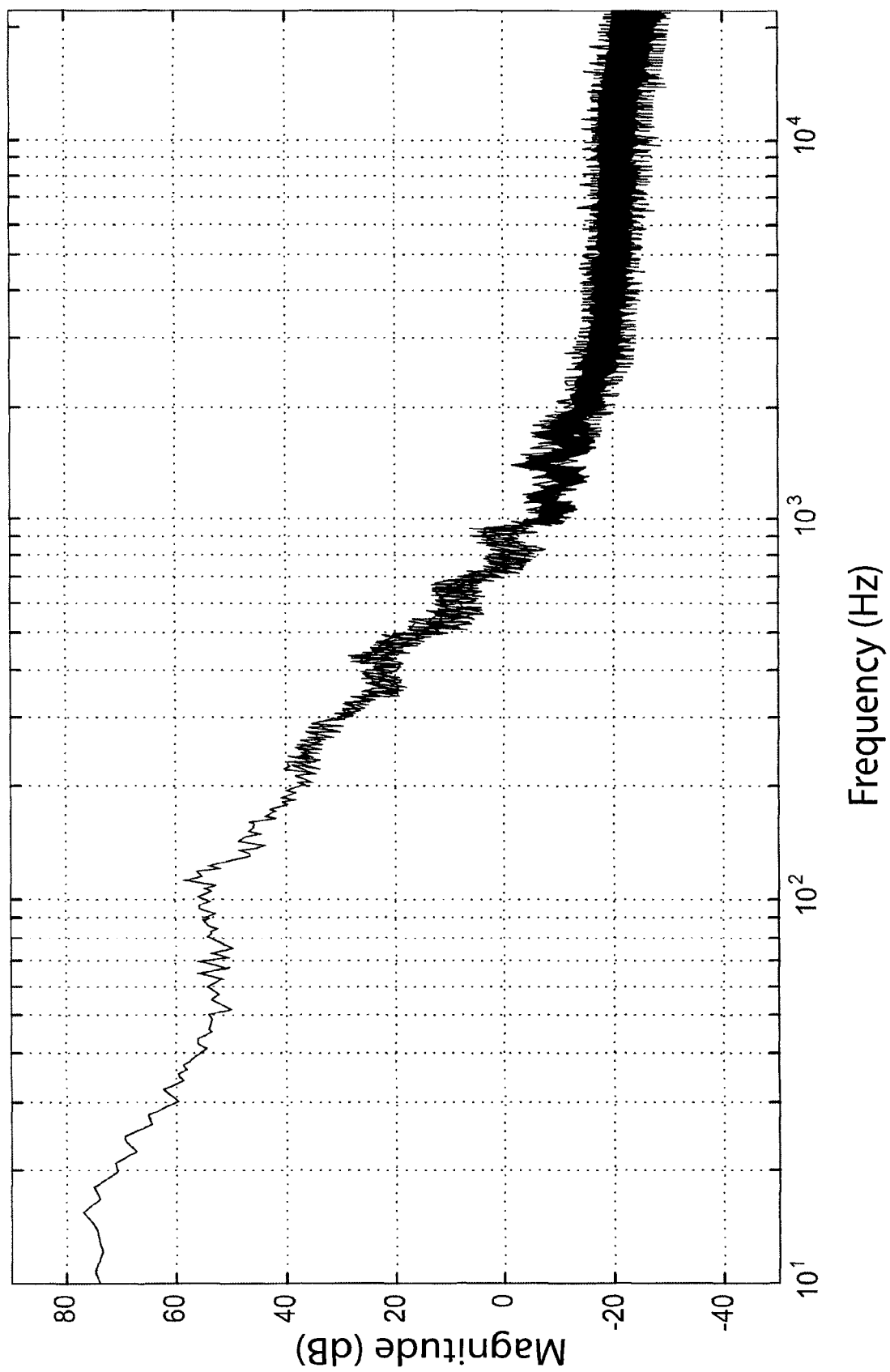
Figure 5:
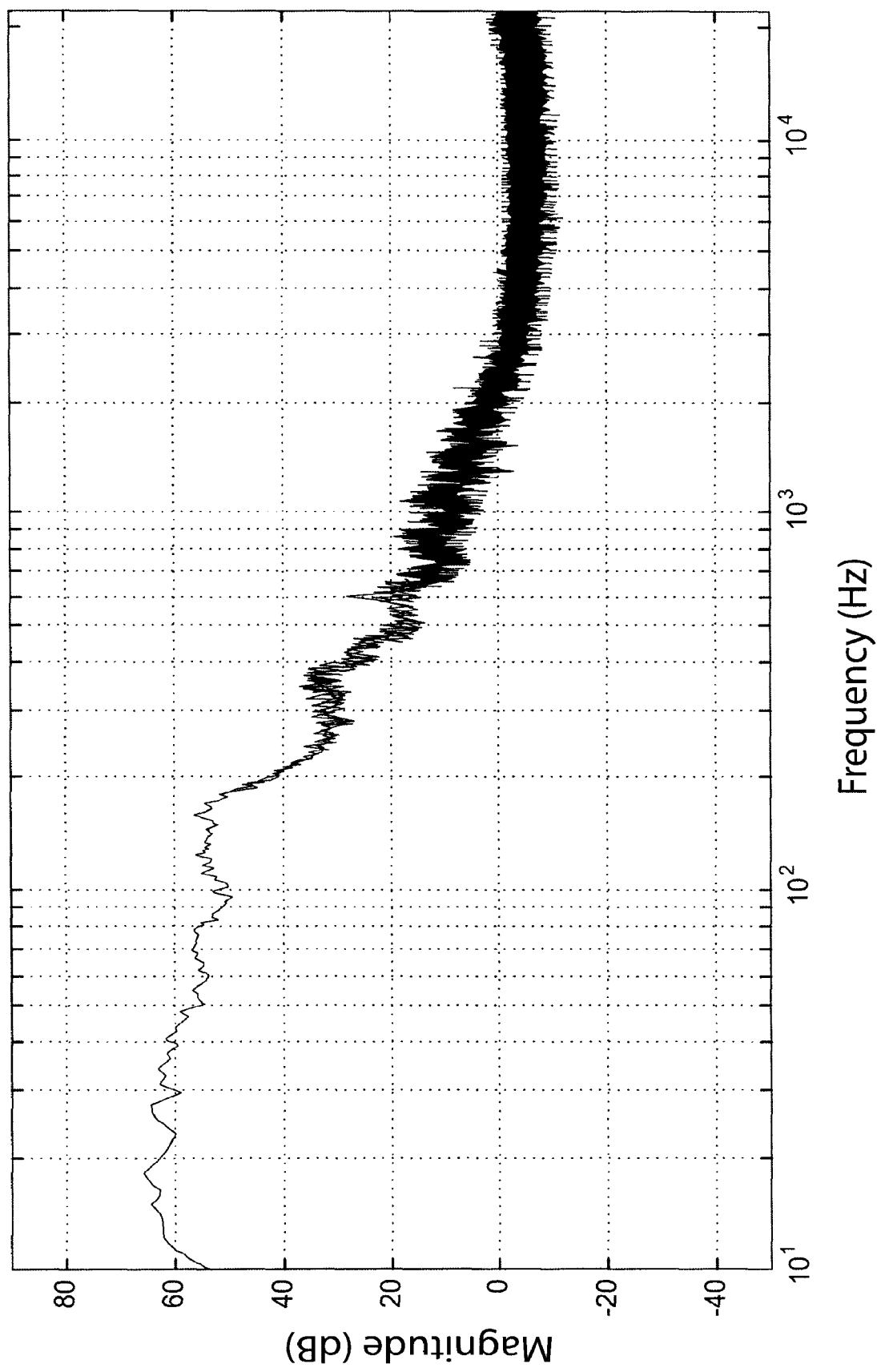

FIGS. 3, 4 and 5 show typical noise generated inside a human body by the intestines, FIG. 3, the respiratory system, FIG. 4, and the heart's beating, FIG. 5.

Suitably, the system 11 comprises a function for cancelling such noises, preferably located in the processing unit 12. The cancellation function is preferably also implemented as a DSP algorithm, and serves to reduce or entirely eliminate the amount of such noise in the input to the command generator.

Figure 6:
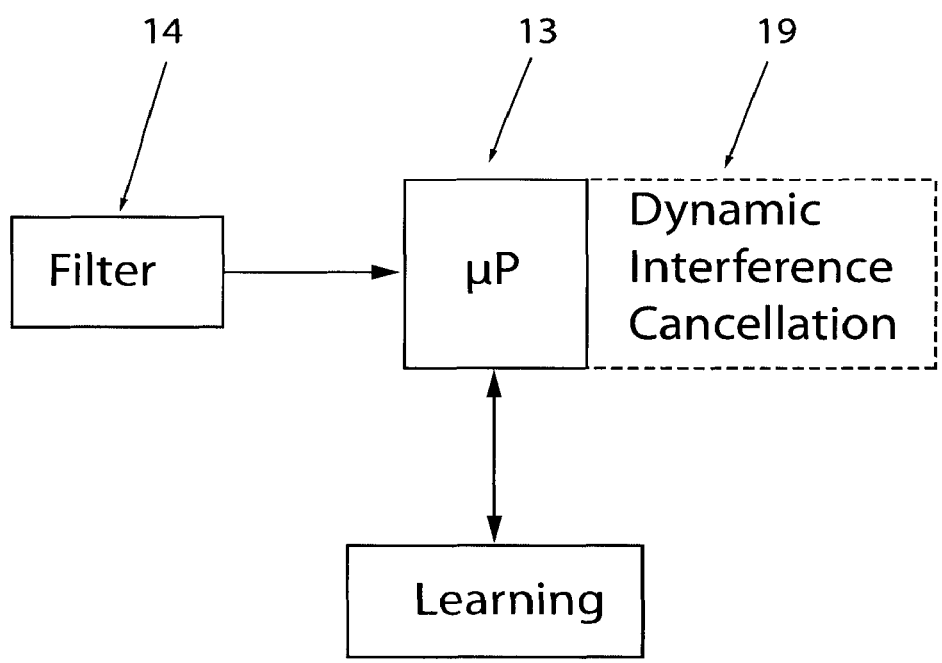
FIG. 6 shows a block diagram of some components of one embodiment of the system of the invention.

This is shown schematically in a block diagram in FIG. 6, which shows a dynamic noise cancellation function 19 attached to the processor 13. Naturally, the cancellation function 17 can either be an integrated part of the processor 16, or it can be a separate component which is connected to the processor 13. The block diagram of FIG. 6 also shows a block for a learning function for learning voice commands, about which more will be said later in this text.

The cancellation function 19 can be activated in a number of ways, in various embodiments of the invention:

In one embodiment, the cancellation function 19 is constantly active, whilst in another embodiment, the cancellation function 19 is adapted to recognize one or more specific noise sources in the mammal body 10, and to activate said cancellation when noise from such a noise source is detected. Thus, in the latter embodiment, the cancellation function 19 can be said to be "sleeping" when there is an absence of internally generated noise in the body 10. The term "absence" should here be taken to mean that such noises are below a predefined threshold, above which the cancellation is activated and carries out its cancelling function.

In a further embodiment, the system 11 comprises a function for recognizing when a user issues spoken commands, and then activates the cancellation function.

Returning now to the issue of the voice recognition function of the system 11, the system 11 will, as mentioned, in one embodiment comprise, suitably in the command generator 16, a learning function which is adapted to perform learning sessions for learning which of a number of voice commands that should be interpreted as meaning one of a number of pre-programmed commands stored in the memory 15.

The learning sessions can be performed before the system 11 is implanted in the patient, in which case the system 11 will be exposed to a number of voice commands, until the learning function has learnt to recognize these commands, at which point in time recognized commands can be associated with a certain command that should be output to the medical implant 17. For example, if one of the commands that have been recognized is "open", an operator will then indicate to the system 11 by means of an interface that the command "open" should result in a certain electrical signal or command being output on the connection 18 to the implant 17.

The learning and recognition can either be such that the learning function learns to recognize commands only from a certain set of individuals who are authorized to operate the medical implant 17, or the learning and recognition can be such that the earning function learns a set of commands to recognize regardless of the identity of the speaker.

Alternatively, or as a complement, the leaning function can also in one embodiment be adapted for learning in situ. In such a case, the system 11 will comprise a wireless receiver for receiving commands from a remote control outside of the mammal body, which commands will comprise commands which should also be generated by the command generator upon recognizing a voice command from a user, so that a voice command issued by a user can be accompanied by a wireless command from the remote control during a learning session, in order for the learning function to learn which command that should be generated upon the reception of a certain voice command.

Using the example of the word "open" again, a user will then set the system in its learning mode, and utter the word "open" a number of times, following which the user will use the remote control to activate the command which should be triggered by the word "open", thus associating that command with the word "open".

Figure 7:
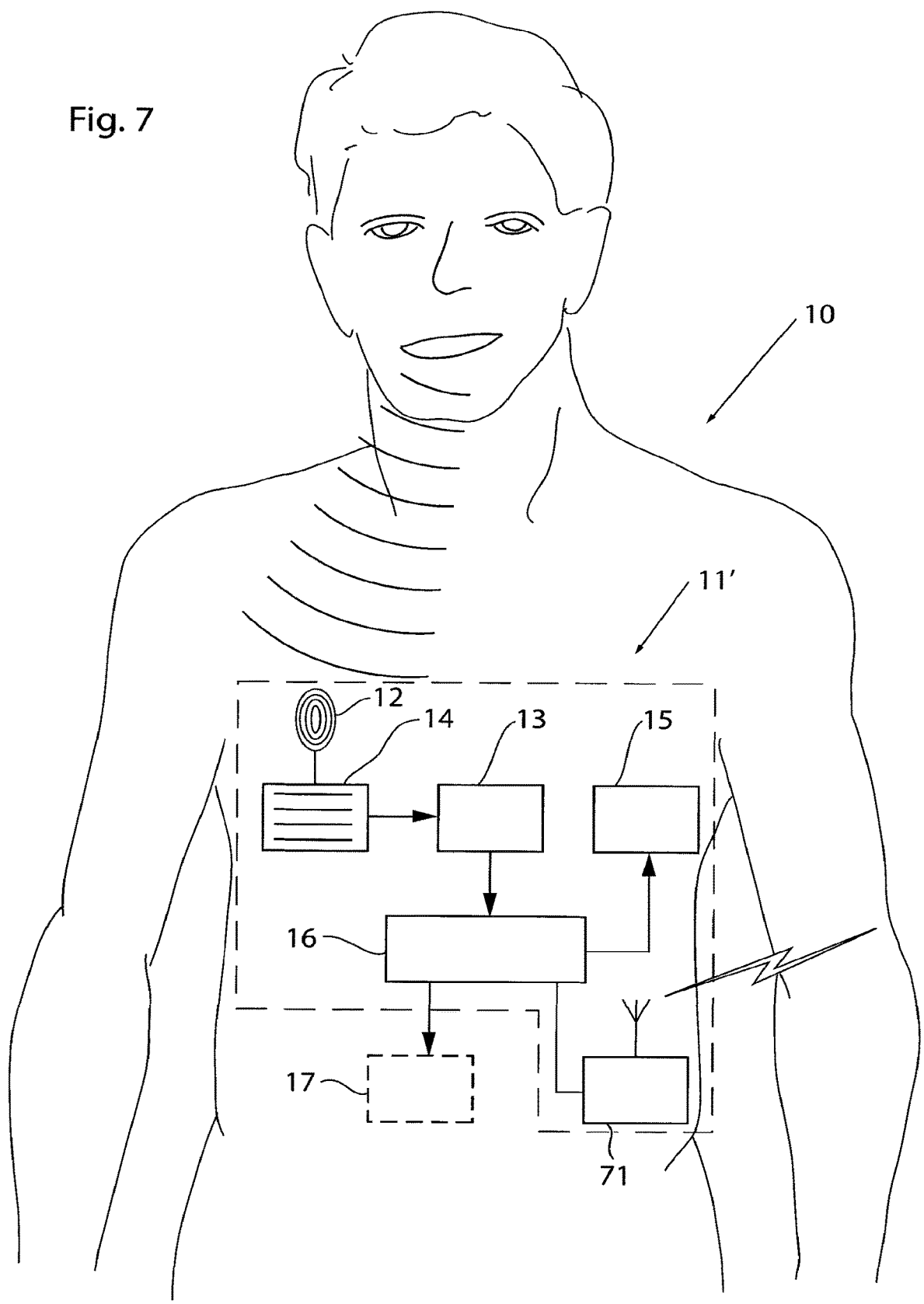
FIG. 7 shows an overview of one embodiment of a system of the invention.

As shown in FIG. 7, as a complement to this procedure, a version 11' of the system can also comprise a wireless transmitter 71, which the learning function is adapted to use in order to signal to a user during a learning session that a voice command has been learnt by the learning function.

Thus, the user can be alerted to the fact that the learning function has learnt the word "open", upon which the user uses a remote control to activate the command which should be associated with that word, and then terminates the learning function, or goes on to teach the learning function another word or phrase.

In those embodiments 11' where the system comprises the wireless transmitter 71 for communicating with a user, such a transmitter 71 can also be used in the following manner: the command generator 16 and/or the processing device 13 comprises means for receiving signals from the medical implant, and the system then uses the transmitter 71 for transmitting said signals to a user. The transmitter in question may, for example, be a radio transmitter or a sonic transmitter. Naturally, the transmitter 71 can also be included in the system even if there is no learning function in the system.

Figure 8:
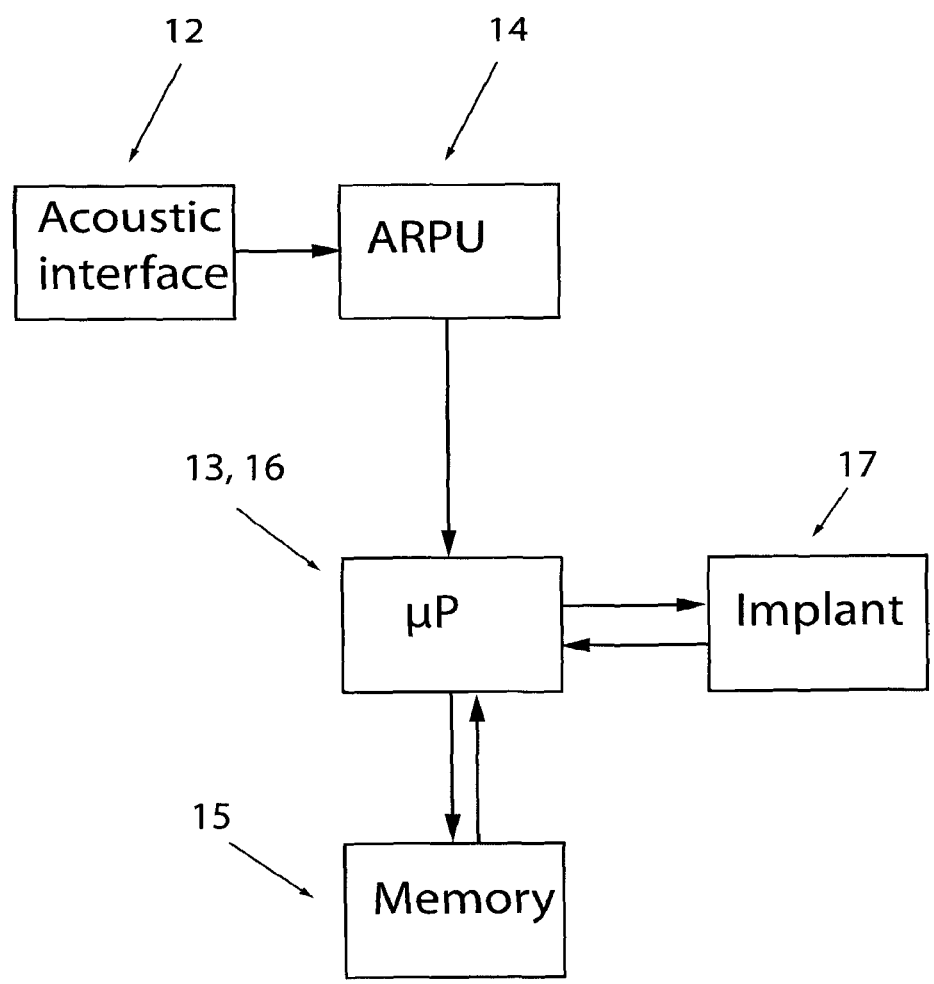
FIG. 8 shows a block diagram of some components of one embodiment of the system of the invention.

FIG. 8 shows an alternative view of hardware that is comprised in the system 11 of the invention.

The hardware shown in FIG. 8 comprises the processing unit 13, the microphone or acoustic transducer 12, and as an alternative to the filter 14 there is shown as so called audio reconstruction unit ARPU 14. The implant 17 is also shown. The processing unit 13 runs software stored in the memory 15, which is a bidirectional memory which can also store other parameters and which can also log parameters. As indicated by means of the reference number 16, the processing unit also serves the role of the command generator illustrated previously, with the aid of the memory 15.

The processing unit can be a microcontroller, a digital signal processor or some other processing device with the ability to run voice recognition software. The processing unit could also be an application specific integrated circuit with hardware support for the voice recognition. The processing unit could also be a combination of the types mentioned above.

As mentioned previously, in some of its embodiments, the inventive system 11 has the ability not only to correct received audio signals for the transfer function of the body and possibly also of a watertight casing, but the system 11 also has the ability to cancel noise caused by the body. This can be the task of the Audio Reconstruction Processing Unit, the ARPU. The ARPU can perform this function in a number of ways, for example by means of low-pass, band-pass, and high-pass filters such as Butterworth, Bessel etc. or more advanced filters such as Sub-band Adaptive Filters, SAF. Sub-band Adaptive filters, SAF, will be described briefly below, with reference to FIG. 9. Sub-band filters first divide the signal into different frequency bands, and then each sub-band is filtered independently. The advantage of this is that the computational cost is lower, and the convergence of the adaptive part of the filter is faster.

Figure 9:
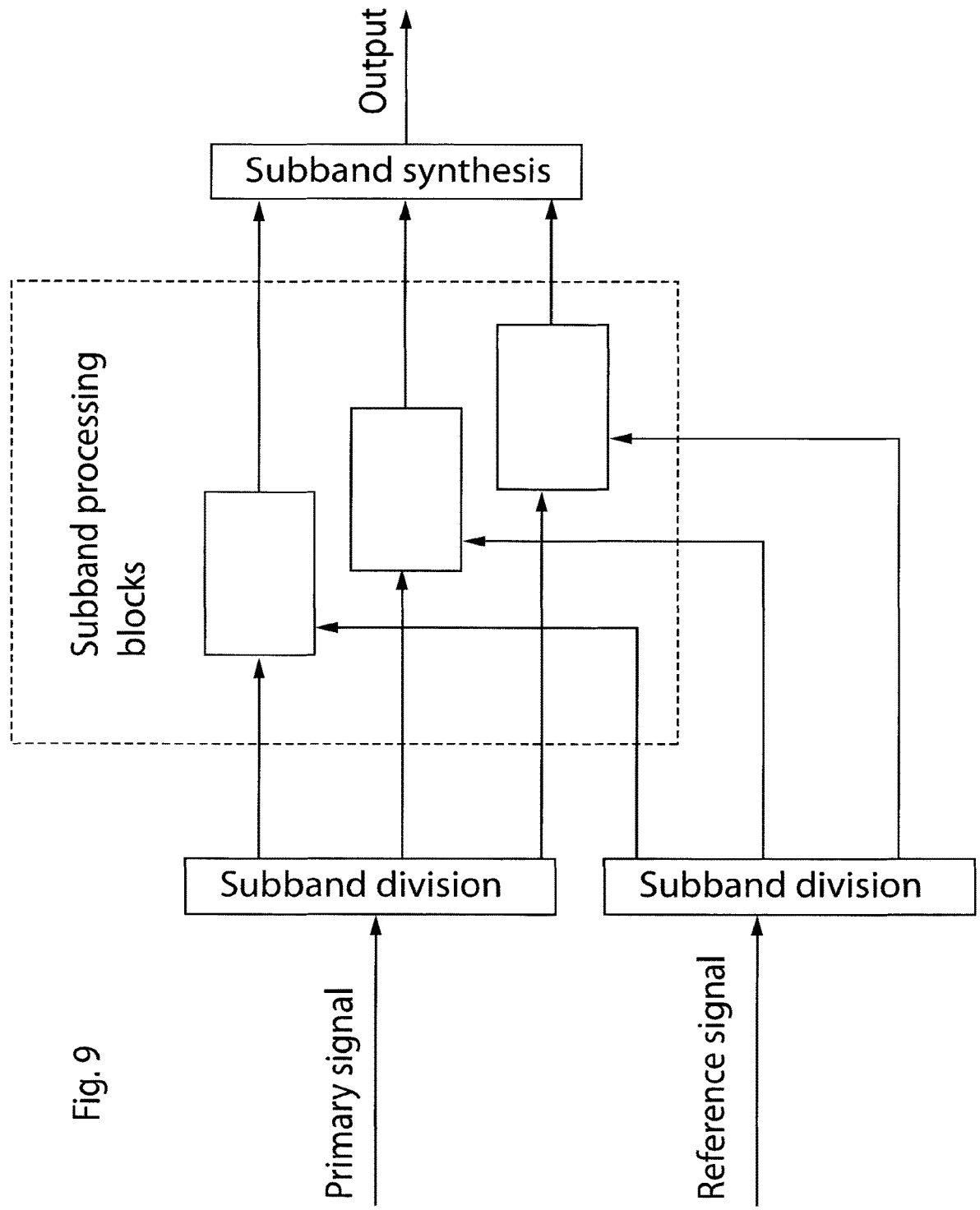
FIGS. 9 and 10 illustrate a filter used in some embodiments of the invention.

FIG. 9 shows a generic sub-band filter, and if the sub-band processing blocks are adaptive, the system is a sub-band adaptive filter. As can be seen in the figure, the filter has two inputs, the primary signal and a reference signal. The primary signal should be the noisy signal containing the speech signal, and the reference signal a signal with mostly coherent noise. A common method of adapting the sub-band processing blocks is the Least Mean Squares method, LMS.

In some applications, it is difficult to place two microphones in such a way that one of them picks up the voice signal, and the other one only picks up coherent noise. To be able to get a good noise cancellation anyway, a Voice Activity Detector, a VAD, can be used. A VAD detects when there is a voice signal present on the primary input, and when this is the case, the adaptive filter halts its adaptation, and the input signal is connected to the primary input. In this manner, one microphone can alter between being the reference and the primary signal.

Figure 10:
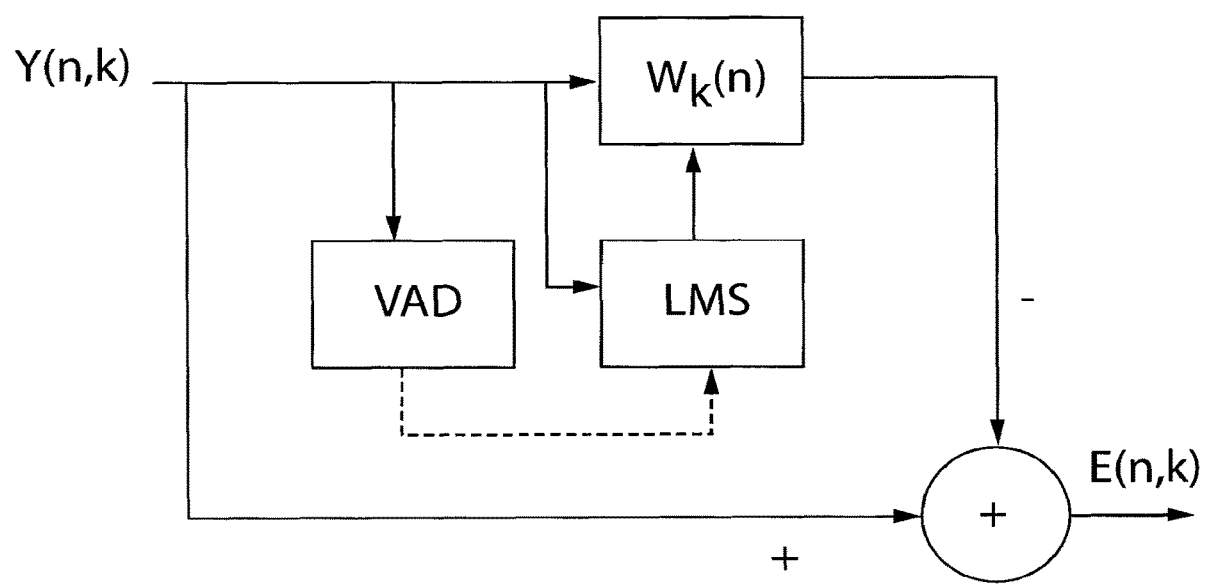

In FIG. 10, a processing block of a sub-band adaptive filter is shown. The estimated noise, $w_k(n)$, is subtracted from the input signal. The noise estimation is based on Least Mean Squares algorithm, and is updated when the VAD signal is inactive.

Regarding the acoustic transducer or microphone 12, one way of improving the overall system performance is to use an array of microphones rather than just one microphone. The filtering techniques can then be based on differences between the received signals; if the transducers are unidirectional, the ARPU and/or the processing unit 13 can determine which signals that are noise and which signals that are the actual voice commands of a speaker, if one of the microphones is directed towards the voice commands or signals, and one microphone is directed in the opposite direction.

Figure 11:
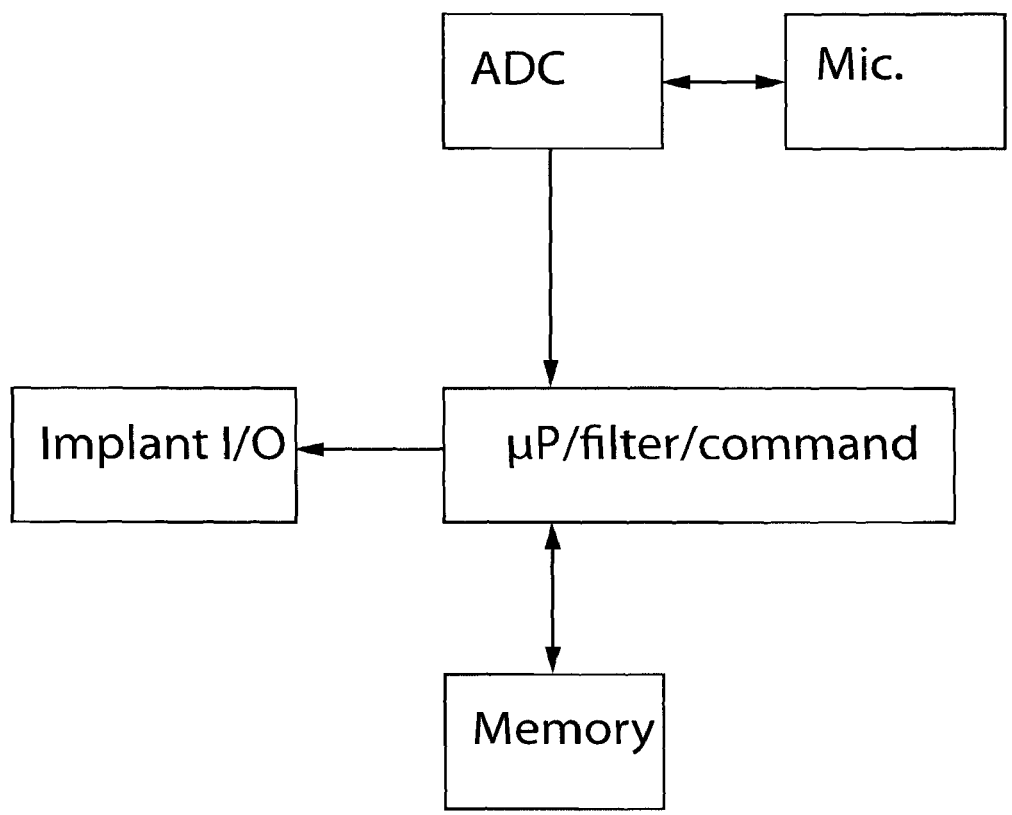
FIG. 11 shows a block diagram of an alternative design of the invention.

FIG. 11 shows a block diagram of another alternative design of the system 11 of the invention. As shown here, there is comprised an ADC, an analogue to digital converter in the system, placed immediately following the command input device 12, here shown as a microphone, "mic". The processing device, the filter and the command generator are here shown as being comprised in one and the same block, such as a processor, for example a micro-processor which interfaces with an I/O-interface in the implant 17 and with a memory. The processing device can be either a so called GP MCU, a general purpose micro controller unit or a so called GP DSP, a general purpose digital signal processor.

Regarding the software which is used in a system 11 of the present invention, it is suitably divided into two parts, the voice recognition and learning algorithms, and the implant control algorithms. The implant control part of the software is suitably be tailored for each implant application for which it is intended.

Turning now to the voice recognition algorithms, there are a number of different ways to implement such algorithms. A received audio command is in one embodiment converted to digital form, as shown above, by means of an ADC, and is then subjected to so called "frame blocking", windowing and FFT, Fast Fourier Transform, where the FFT is used in order to obtain a representation of the signal in the frequency domain.

As an example, the signal which is obtained by means of the FFT can also be exposed to so called feature extraction, following which the signal is subjected to pattern matching, to match a received command with stored commands, in order to see if the received command exhibits a sufficient likeness to one of a set of stored commands. The term "sufficient likeness" is here used to signify that a threshold is suitably used for the comparison.

As examples of pattern matching algorithms, the following can be mentioned:
Dynamic Time Warping
Hidden Markov Models
Artificial Neural Networks
Vector Quantization As has been mentioned previously, the speech recognition can be either speaker dependent or speaker independent. If the recognition is speaker dependent or speaker independent depends mainly on if the recognition engine is trained with different speakers or just one. It is however also possible to change the features used, and to optimize the pattern matching method for either speaker dependent or speaker independent recognition.

Before speaker dependent recognition can be done, the system has to learn the characteristics of the speaker's voice. This is done during a training phase where the speaker utters each of the different commands a few times, so that the recognition software can adapt the pattern matching variables according to that specific speaker.

Figure 12:
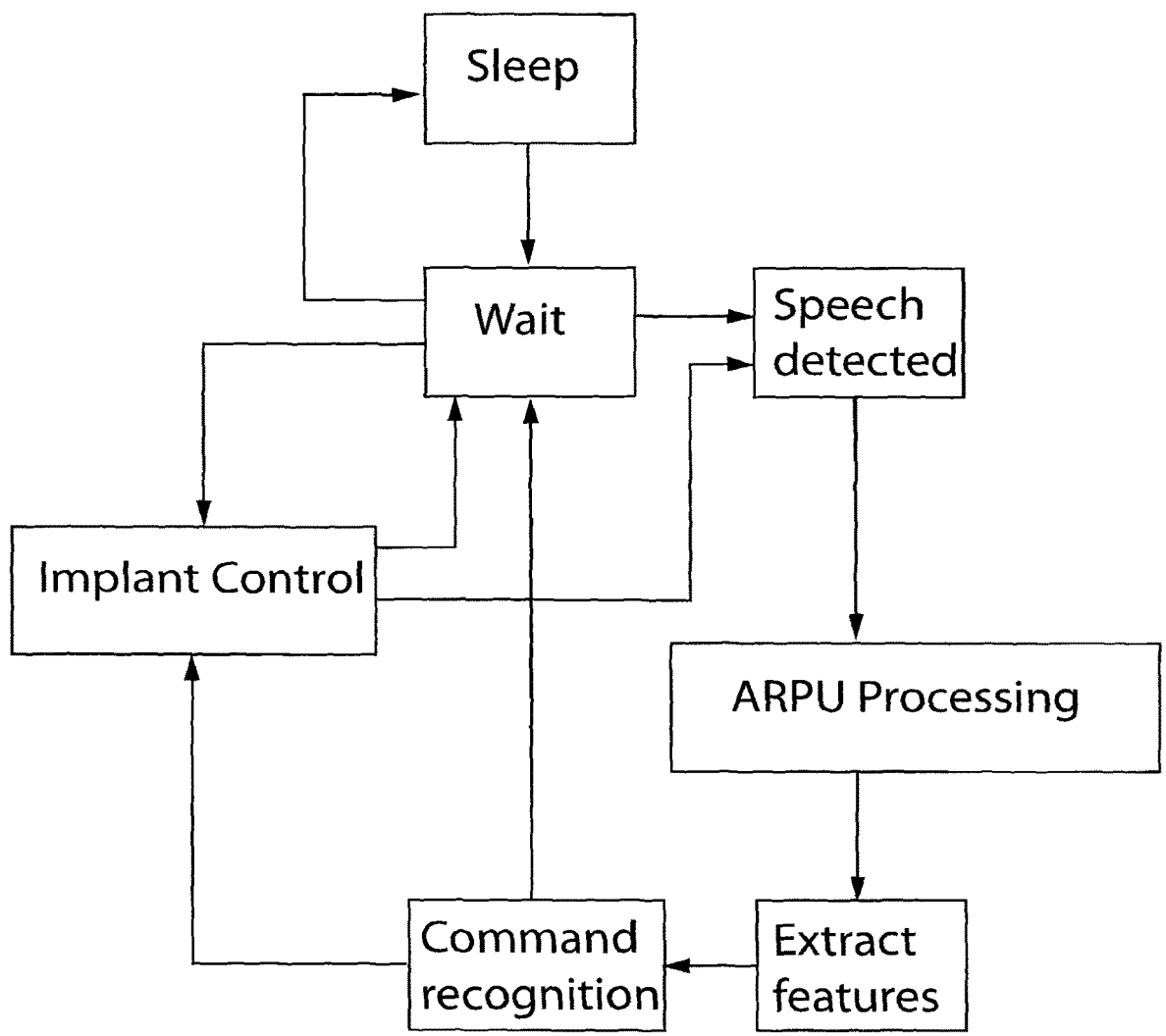
FIG. 12 shows a state diagram.

A state diagram for different states which can be assumed by the voice recognition part of the software of the present invention is shown in FIG. 12, and described briefly below:

The implant is in Sleep mode to preserve energy when it doesn't perform any other tasks. It leaves the sleep state when an "awake event" is received and goes to the wait state. From the wait state, the implant either performs controlling of the implant and returns to the wait state, or it can have received an "audio wake-up event", if speech has been detected and then processed by the ARPU, and is determined to be a valid command from a validated speaker, the command is executed, and the program returns to the wait state. From the wait state, the implant returns to sleep mode if no more tasks is to be done, and no more voice commands are given.

Figure 13:
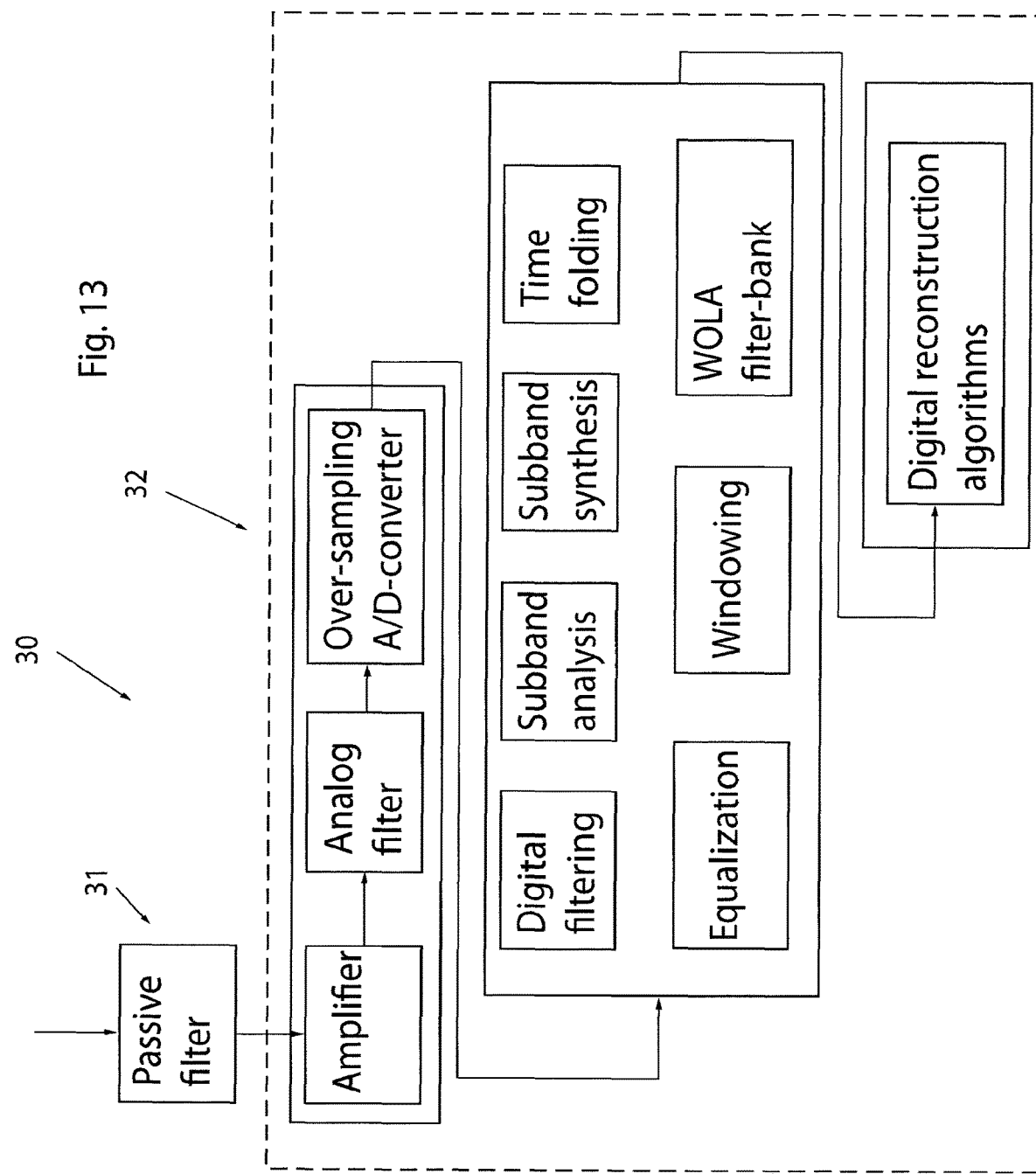
FIG. 13 shows a block diagram of a possible component used in the invention.

As mentioned, in one embodiment the inventive system makes use of a so called ARPU, an Audio Reconstruction Processing Unit. A block diagram of a possible such ARPU 32 is shown in FIG. 13. The ARPU is shown as comprising a passive filter 31 which receives its input from an audio input device, and a generic DSP 32, about which the following can be said:

The DSP 32 comprises an analogue input, to which the signals from the filter 31 are connected. There the analogue signal is amplified, and more post amplification filtering can be done before the signal is quantized by a sigma-delta analogue-to-digital converter. A WOLA filter bank can then perform a number of different operations, including digital filtering, either by traditional IIR/FIR filters or by more advanced filters, such as sub-band adaptive filters.

The filtering, analysis and synthesis can be done on sub-bands to decrease computational complexity and to increase convergence rates on adaptive filters. Since the filter-bank is highly over-sampled, the alias effects of the sub-bands are small. A windowing function can be applied to minimize signal discontinuities in the beginning and end of the sample. Other examples of operations that can be made in the filter-bank includes time folding and equalization.

The system of the invention needs to be powered, which can be done in a number of ways, some of which will be described in the following.

Figure 14:
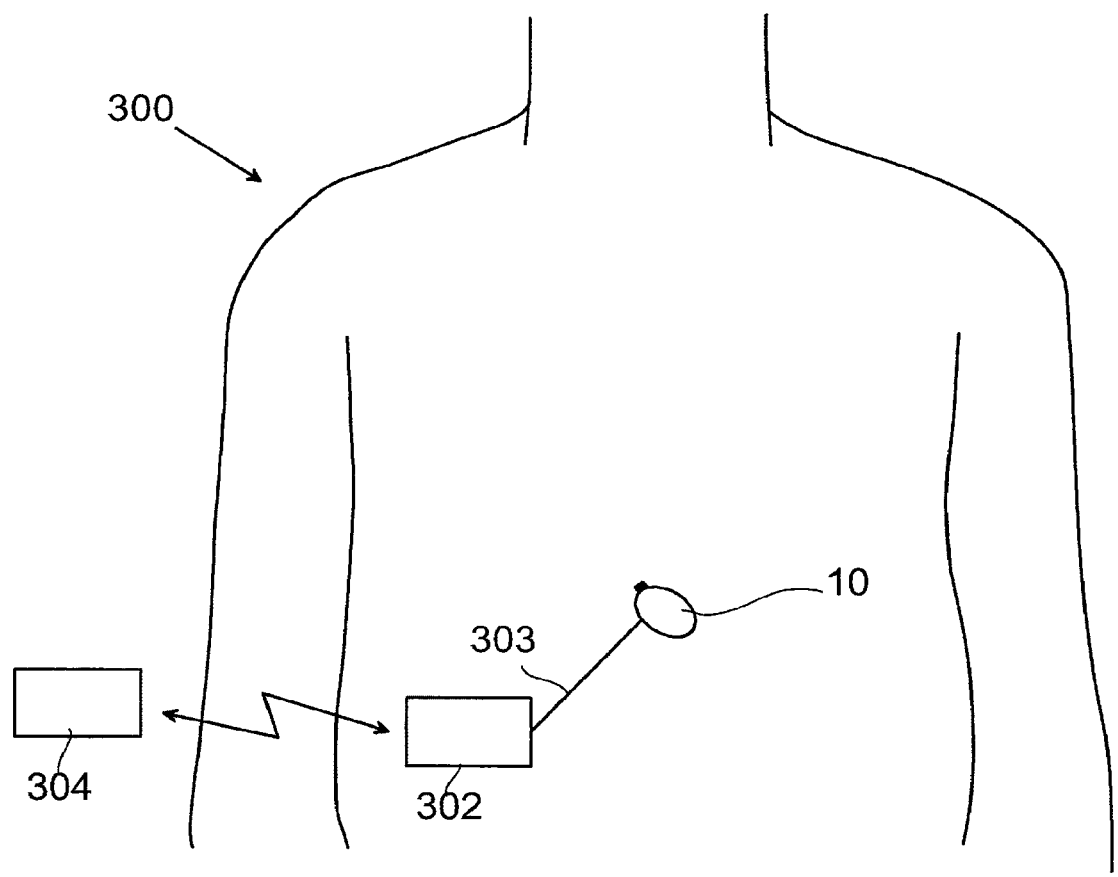
FIGS. 14-26 show various embodiments of solutions for powering the system of the invention.

The system of the invention will also be referred to below as "the apparatus". FIG. 14 illustrates one embodiment of a system 300 for supplying the first system of the present invention with energy, with the inventive system here being given the reference number 10. The system 10 is, by way of example, in FIG. 14 shown as being placed in the abdomen of a patient; the implant which is to be controlled via the system 10 is not shown in FIG. 14.

In one embodiment, an implantable energy-transforming device 302 is adapted to supply energy consuming components of the apparatus 10 with energy via a power supply line 303. An external energy-transmission device 304 for non-invasively energizing the apparatus 10 transmits energy to the implantable energy-transforming device 302 by at least one wireless energy signal. The implanted energy-transforming device 302 transforms energy from the wireless energy signal into electrical energy which is supplied via the power supply line 303.

The wireless energy signal may include a wave signal selected from the following: a sound wave signal, an ultrasound wave signal, an electromagnetic wave signal, an infrared light signal, a visible light signal, an ultra violet light signal, a laser light signal, a micro wave signal, a radio wave signal, an x-ray radiation signal and a gamma radiation signal. Alternatively, the wireless energy signal may include an electric or magnetic field, or a combined electric and magnetic field.

The wireless energy-transmission device 304 may transmit a carrier signal for carrying the wireless energy signal. Such a carrier signal may include digital, analogue or a combination of digital and analogue signals. In this case, the wireless energy signal includes an analogue or a digital signal, or a combination of an analogue and digital signal.

Generally speaking, the energy-transforming device 302 is provided for transforming wireless energy of a first form transmitted by the energy-transmission device 304 into energy of a second form, which typically is different from the energy of the first form. The implanted apparatus 10 is operable in response to the energy of the second form. The energy-transforming device 302 may directly power the apparatus with the second form energy, as the energy-transforming device 302 transforms the first form energy transmitted by the energy-transmission device 304 into the second form energy. The system may further include an implantable accumulator, wherein the second form energy is used at least partly to charge the accumulator.

Alternatively, the wireless energy transmitted by the energy-transmission device 304 may be used to directly power the apparatus 10, as the wireless energy is being transmitted by the energy-transmission device 304. Where the system comprises an operation device for operating the apparatus, as will be described below, the wireless energy transmitted by the energy-transmission device 304 may be used to directly power the operation device to create kinetic energy for the operation of the apparatus.

The wireless energy of the first form may comprise sound waves and the energy-transforming device 302 may include a piezo-electric element for transforming the sound waves into electric energy. The energy of the second form may comprise electric energy in the form of a direct current or pulsating direct current, or a combination of a direct current and pulsating direct current, or an alternating current or a combination of a direct and alternating current. Normally, the apparatus comprises electric components that are energized with electrical energy. Other implantable electric components of the system may be at least one voltage level guard or at least one constant current guard connected with the electric components of the apparatus.

Optionally, one of the energy of the first form and the energy of the second form may comprise magnetic energy, kinetic energy, sound energy, chemical energy, radiant energy, electromagnetic energy, photo energy, nuclear energy or thermal energy. Preferably, one of the energy of the first form and the energy of the second form is non-magnetic, non-kinetic, non-chemical, non-sonic, non-nuclear or non-thermal.

The energy-transmission device may be controlled from outside the patient's body to release electromagnetic wireless energy, and the released electromagnetic wireless energy is used for operating the apparatus.

Alternatively, the energy-transmission device is controlled from outside the patient's body to release non-magnetic wireless energy, and the released non-magnetic wireless energy is used for operating the apparatus.

The external energy-transmission device 304 can also, in one embodiment, include a wireless remote control having an external signal transmitter for transmitting a wireless control signal for non-invasively controlling the apparatus. The control signal is received by an implanted signal receiver which may be incorporated in the implanted energy-transforming device 302 or be separate there from.

The wireless control signal may include a frequency, amplitude, or phase modulated signal or a combination thereof. Alternatively, the wireless control signal includes an analogue or a digital signal, or a combination of an analogue and digital signal. Alternatively, the wireless control signal comprises an electric or magnetic field, or a combined electric and magnetic field.

The wireless remote control may transmit a carrier signal for carrying the wireless control signal. Such a carrier signal may include digital, analogue or a combination of digital and analogue signals. Where the control signal includes an analogue or a digital signal, or a combination of an analogue and digital signal, the wireless remote control preferably transmits an electromagnetic carrier wave signal for carrying the digital or analogue control signals.

Figure 15:
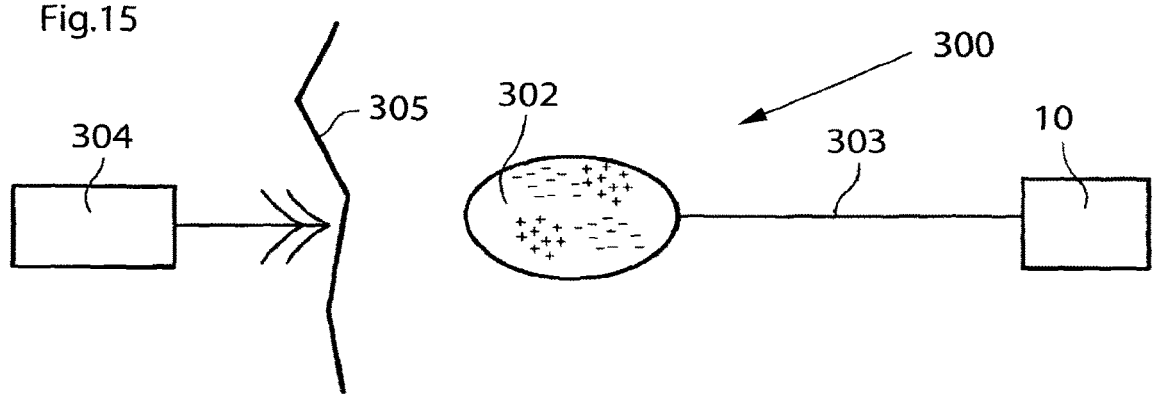

FIG. 15 illustrates the system of FIG. 4 in the form of a more generalized block diagram showing the system 10, the energy-transforming device 302 powering the apparatus 10 via power supply line 303, and the external energy-transmission device 304, The patient's skin 305, generally shown by a vertical line, separates the interior of the patient to the right of the line from the exterior to the left of the line.

Figure 16:
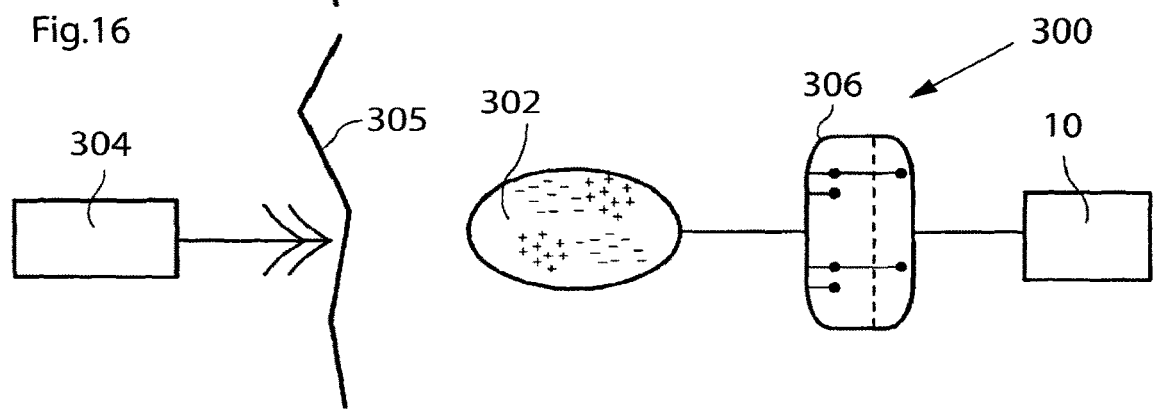

FIG. 16 shows an embodiment of the invention identical to that of FIG. 15, except that a reversing device in the form of an electric switch 306 operable for example by polarized energy also is implanted in the patient for reversing the apparatus or system 10. When the switch is operated by polarized energy, the wireless remote control of the external energy-transmission device 304 transmits a wireless signal that carries polarized energy and the implanted energy-transforming device 302 transforms the wireless polarized energy into a polarized current for operating the electric switch 306. When the polarity of the current is shifted by the implanted energy-transforming device 302 the electric switch 306 reverses the function performed by the apparatus 10.

In all of the embodiments described herein, the energy-transforming device 302 may include a rechargeable accumulator like a battery or a capacitor to be charged by the wireless energy and supplies energy for any energy consuming part of the system.

Figure 17:
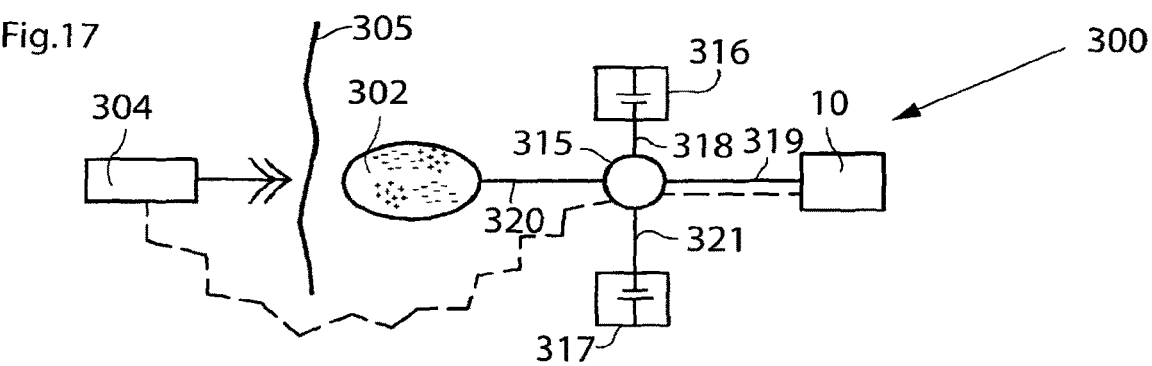

FIG. 17 shows an embodiment of the invention comprising the external energy-transmission device 304, the apparatus 10, the implanted energy-transforming device 302, an implanted internal control unit 315 controlled by the wireless remote control of the external energy-transmission device 304, an implanted accumulator 316 and an implanted capacitor 317.

The internal control unit 315 arranges storage of electric energy received from the implanted energy-transforming device 302 in the accumulator 316, which supplies energy to the apparatus 10. In response to a control signal from the wireless remote control of the external energy-transmission device 304, the internal control unit 315 either releases electric energy from the accumulator 316 and transfers the released energy via power lines 318 and 319, or directly transfers electric energy from the implanted energy-transforming device 302 via a power line 320, the capacitor 317, which stabilizes the electric current, a power line 321 and the power line 319, for the operation of the apparatus 10.

The internal control unit is preferably programmable from outside the patient's body. In a preferred embodiment, the internal control unit is programmed to regulate the apparatus 10 according to a pre-programmed time-schedule or to input from any sensor sensing any possible physical parameter of the patient or any functional parameter of the system.

In accordance with an alternative, the capacitor 317 in the embodiment of FIG. 17 may be omitted. In accordance with another alternative, the accumulator 316 in this embodiment may be omitted.

Figure 18:
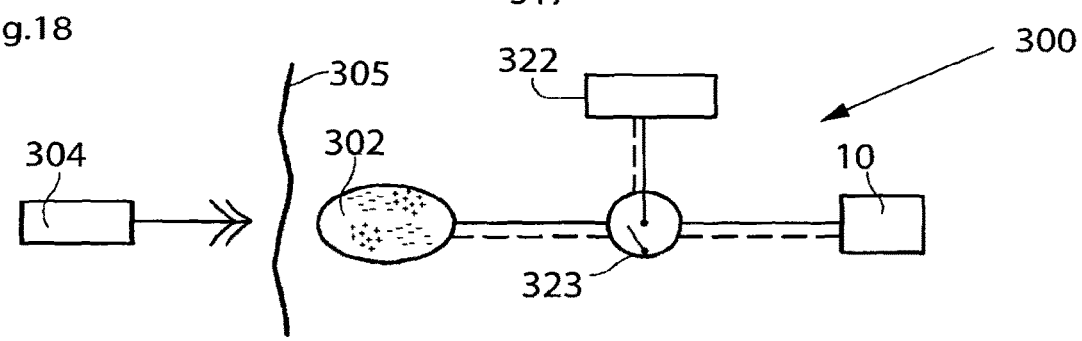

FIG. 18 shows an embodiment of the invention identical to that of FIG. 15, except that a battery 322 for supplying energy for the operation of the apparatus 10 and an electric switch 323 for switching the operation of the apparatus 10 are also implanted in the patient. The electric switch 323 may be controlled by the remote control and may also be operated by the energy supplied by the implanted energy-transforming device 302 to switch from an off mode, in which the battery 322 is not in use, to an on mode, in which the battery 322 supplies energy for the operation of the apparatus 10.

Figure 19:
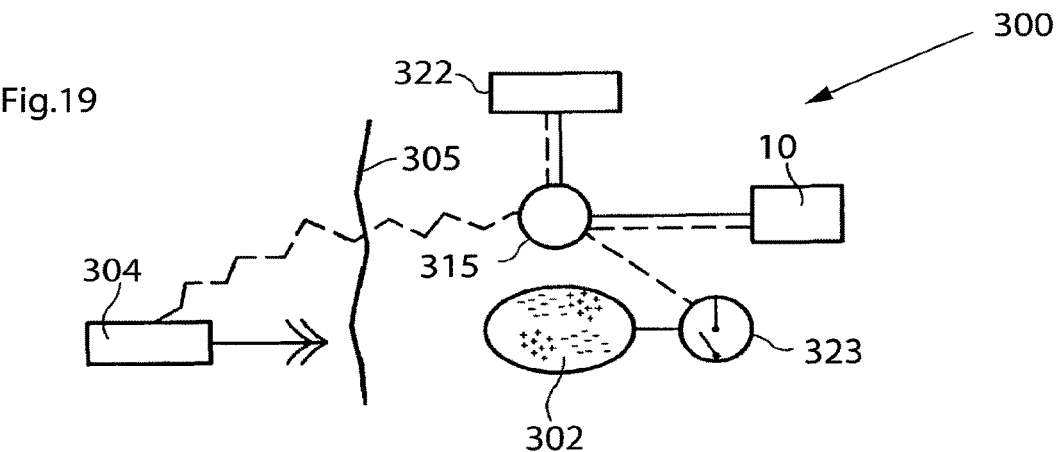

FIG. 19 shows an embodiment of the invention identical to that of FIG. 18, except that an internal control unit 315 controllable by a wireless remote control of the external energy-transmission device 304 also is implanted in the patient. In this case, the electric switch 323 is operated by the energy supplied by the implanted energy-transforming device 302 to switch from an off mode, in which the wireless remote control is prevented from controlling the internal control unit 315 and the battery is not in use, to a standby mode, in which the remote control is permitted to control the internal control unit 315 to release electric energy from the battery 322 for the operation of the apparatus 10.

Figure 20:
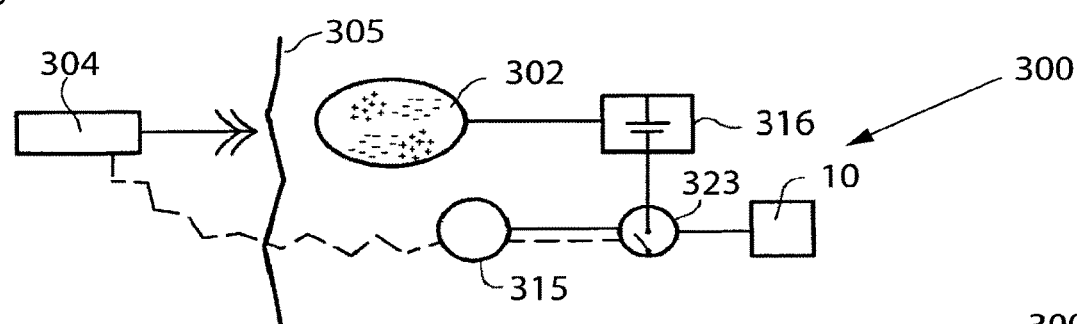

FIG. 20 shows an embodiment of the invention identical to that of FIG. 19, except that an accumulator 316 is substituted for the battery 322 and the implanted components are interconnected differently. In this case, the accumulator 316 stores energy from the implanted energy-transforming device 302. In response to a control signal from the wireless remote control of the external energy-transmission device 304, the internal control unit 315 controls the electric switch 323 to switch from an off mode, in which the accumulator 316 is not in use, to an on mode, in which the accumulator 316 supplies energy for the operation of the apparatus 10. The accumulator may be combined with or replaced by a capacitor.

Figure 21:
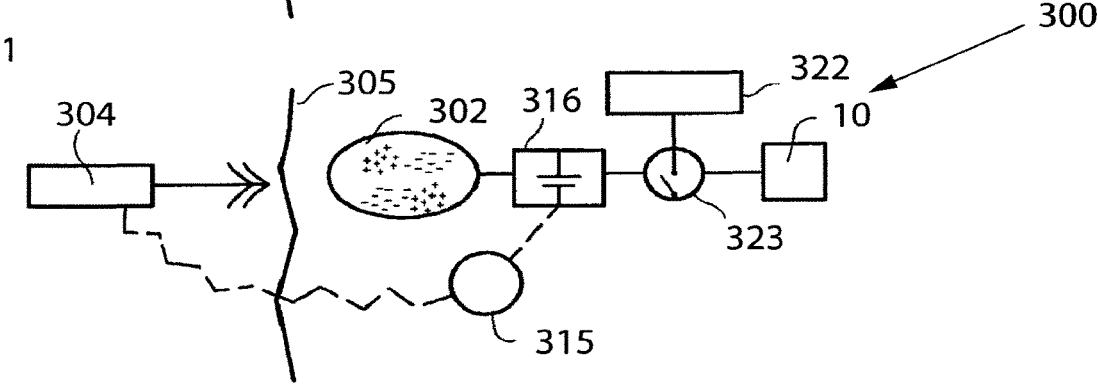

FIG. 21 shows an embodiment of the invention identical to that of FIG. 20, except that a battery 322 also is implanted in the patient and the implanted components are interconnected differently. In response to a control signal from a wireless remote control of the external energy-transmission device 304, the internal control unit 315 controls the accumulator 316 to deliver energy for operating the electric switch 323 to switch from an off mode, in which the battery 322 is not in use, to an on mode, in which the battery 322 supplies electric energy for the operation of the apparatus 10.

Alternatively, the electric switch 323 may be operated by energy supplied by the accumulator 316 to switch from an off mode, in which the wireless remote control is prevented from controlling the battery 322 to supply electric energy and is not in use, to a standby mode, in which the wireless remote control is permitted to control the battery 322 to supply electric energy for the operation of the apparatus 10.

It should be understood that the switch 323 and all other switches in this application should be interpreted in its broadest embodiment. This means a transistor, MCU, MCPU, ASIC, FPGA or a DA converter or any other electronic component or circuit that may switch the power on and off. Preferably the switch is controlled from outside the body, or alternatively by an implanted internal control unit.

Figure 22:
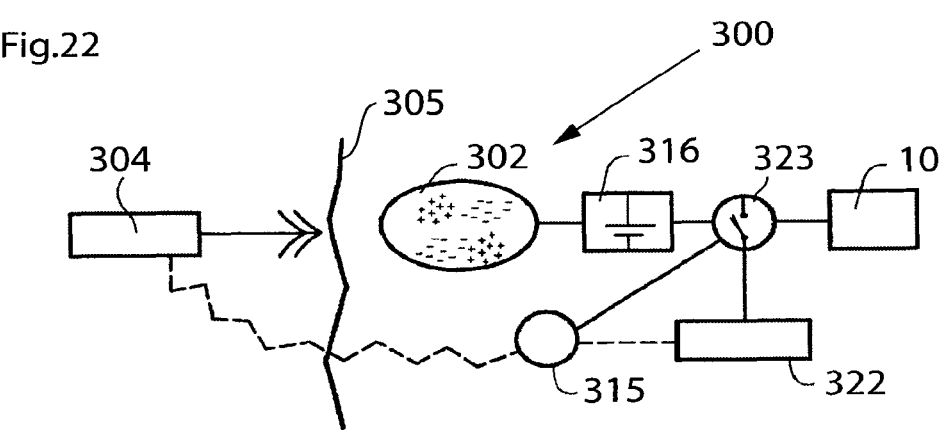

FIG. 22 shows an embodiment of the invention identical to that of FIG. 19 except that the implanted components are interconnected differently. Thus, in this case, the internal control unit 315 is powered by the battery 322 when the accumulator 316, suitably a capacitor, activates the electric switch 323 to switch to an "on" mode. When the electric switch 323 is in its "on" mode, the internal control unit 315 is permitted to control the battery 322 to supply, or not supply, energy for the operation of the apparatus 10.

Figure 23:
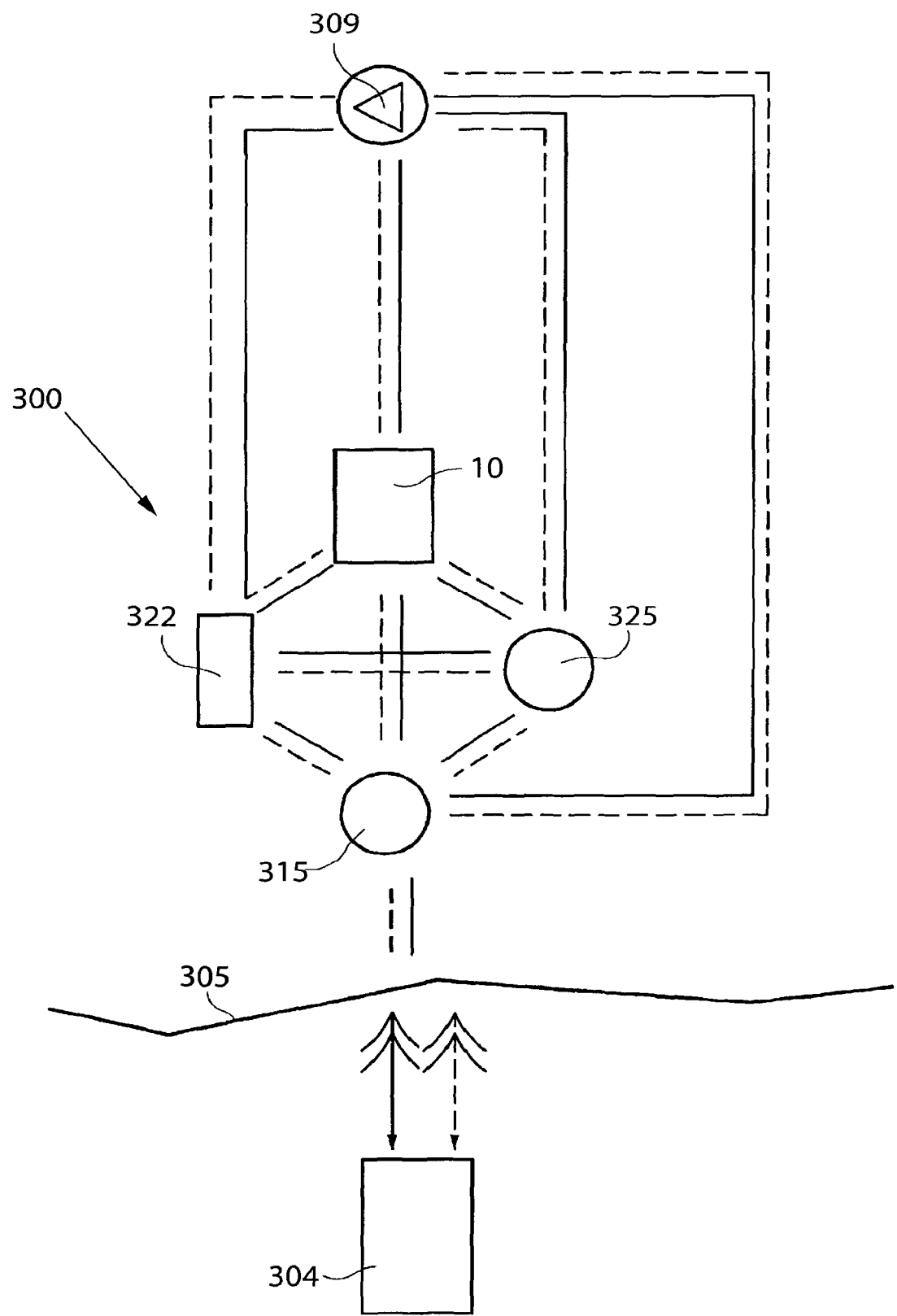

FIG. 23 schematically shows conceivable combinations of implanted components of the apparatus for achieving various communication options. Basically, there is the apparatus 10, the internal control unit 315, an optional component 309, and the external energy-transmission device 304 including the external wireless remote control. As already described above, a wireless remote control transmits a control signal which is received by the internal control unit 315, which in turn controls the various implanted components of the apparatus.

The internal control unit 315, or alternatively the external wireless remote control of the external energy-transmission device 304, may control the apparatus 10 in response to signals from the sensor 325. A transceiver may be combined with the sensor 325 for sending information on the sensed physical parameter to the external wireless remote control. The wireless remote control may comprise a signal transmitter or transceiver and the internal control unit 315 may comprise a signal receiver or transceiver.

Alternatively, the wireless remote control may comprise a signal receiver or transceiver and the internal control unit 315 may comprise a signal transmitter or transceiver. The above transceivers, transmitters and receivers may be used for sending information or data related to the apparatus 10 from inside the patient's body to the outside thereof.

Where the battery 322 for powering the apparatus 10 is implanted, information related to the charging of the battery 322 may be fed back. To be more precise, when charging a battery or accumulator with energy, feedback information related to said charging process is sent and the energy supply is changed accordingly. This information is suitably sent via the communication between the first and second parts of the inventive system.

An internal energy receiver can be adapted to directly or indirectly supply received energy to the energy consuming components of the apparatus 10 via a switch 326. An energy balance is determined between the energy received by the internal energy receiver 302 and the energy used for the apparatus 10, and the transmission of wireless energy is then controlled based on the determined energy balance. The energy balance thus provides an accurate indication of the correct amount of energy needed, which is sufficient to operate the apparatus 10 properly, but without causing undue temperature rise.

In FIGS. 15-22, the patient's skin is indicated by a vertical line 305. Here, the energy receiver comprises an energy-transforming device 302 located inside the patient, preferably just beneath the patient's skin 305. Generally speaking, the implanted energy-transforming device 302 may be placed in the abdomen, thorax, muscle fascia (e.g. in the abdominal wall), subcutaneously, or at any other suitable location. The implanted energy-transforming device 302 is adapted to receive wireless energy E transmitted from the external energy-source 304a provided in an external energy-transmission device 304 located outside the patient's skin 305 in the vicinity of the implanted energy-transforming device 302.

As is well known in the art, the wireless energy E may generally be transferred by means of any suitable Transcutaneous Energy Transfer (TET) device, such as a device including a primary coil arranged in the external energy source 304a and an adjacent secondary coil arranged in the implanted energy-transforming device 302. When an electric current is fed through the primary coil, energy in the form of a voltage is induced in the secondary coil which can be used to power the implanted energy consuming components of the apparatus, e.g. after storing the incoming energy in an implanted energy source, such as a rechargeable battery or a capacitor.

However, the present invention is generally not limited to any particular energy transfer technique, TET devices or energy sources, and any kind of wireless energy may be used. The amount of energy received by the implanted energy receiver may be compared with the energy used by the implanted components of the apparatus. The term "energy used" is then understood to include also energy stored by implanted components of the apparatus.

A control device includes an external control unit that controls the external energy source 304a based on the determined energy balance to regulate the amount of transferred energy. In order to transfer the correct amount of energy, the energy balance and the required amount of energy is determined by means of a determination device including an implanted internal control unit 315 connected between the switch 326 and the apparatus 10. The internal control unit 315 may thus be arranged to receive various measurements obtained by suitable sensors or the like, not shown, measuring certain characteristics of the apparatus 10, somehow reflecting the required amount of energy needed for proper operation of the apparatus 10.

Moreover, the current condition of the patient may also be detected by means of suitable measuring devices or sensors, in order to provide parameters reflecting the patient's condition. Hence, such characteristics and/or parameters may be related to the current state of the apparatus 10, such as power consumption, operational mode and temperature, as well as the patient's condition reflected by parameters such as; body temperature, blood pressure, heartbeats and breathing. Other kinds of physical parameters of the patient and functional parameters of the device are described elsewhere.

Furthermore, an energy source in the form of an accumulator 316 may optionally be connected to the implanted energy-transforming device 302 via the control unit 315 for accumulating received energy for later use by the apparatus 10. Alternatively or additionally, characteristics of such an accumulator, also reflecting the required amount of energy, may be measured as well. The accumulator may be replaced by a rechargeable battery, and the measured characteristics may be related to the current state of the battery, any electrical parameter such as energy consumption voltage, temperature, etc. In order to provide sufficient voltage and current to the apparatus 10, and also to avoid excessive heating, it is clearly understood that the battery should be charged optimally by receiving a correct amount of energy from the implanted energy-transforming device 302, i.e. not too little or too much. The accumulator may also be a capacitor with corresponding characteristics.

For example, battery characteristics may be measured on a regular basis to determine the current state of the battery, which then may be stored as state information in a suitable storage means in the internal control unit 315. Thus, whenever new measurements are made, the stored battery state information can be updated accordingly. In this way, the state of the battery can be "calibrated" by transferring a correct amount of energy, so as to maintain the battery in an optimal condition.

Thus, the internal control unit 315 of the determination device is adapted to determine the energy balance and/or the currently required amount of energy, (either energy per time unit or accumulated energy) based on measurements made by the above-mentioned sensors or measuring devices of the apparatus 10, or the patient, or an implanted energy source if used, or any combination thereof. The internal control unit 315 is further connected to an internal signal transmitter 327, arranged to transmit a control signal reflecting the determined required amount of energy, to an external signal receiver 304c connected to the external control unit 304b. The amount of energy transmitted from the external energy source 304a may then be regulated in response to the received control signal.

Alternatively, the determination device may include the external control unit 304b. In this alternative, sensor measurements can be transmitted directly to the external control unit 304b wherein the energy balance and/or the currently required amount of energy can be determined by the external control unit 304b, thus integrating the above-described function of the internal control unit 315 in the external control unit 304b. In that case, the internal control unit 315 can be omitted and the sensor measurements are supplied directly to the internal signal transmitter 327 which sends the measurements over to the external signal receiver 304c and the external control unit 304b.

The energy balance and the currently required amount of energy can then be determined by the external control unit 304b based on those sensor measurements.

Hence, the present solution can employ the feedback of information indicating the required energy, which is more efficient than many other solutions since it is based on the actual use of energy that is compared to the received energy, e.g. with respect to the amount of energy, the energy difference, or the energy receiving rate as compared to the energy rate used by implanted energy consuming components of the apparatus. The apparatus may use the received energy either for consuming or for storing the energy in an implanted energy source or the like. The different parameters discussed above would thus be used if relevant and needed and then as a tool for determining the actual energy balance. However, such parameters may also be needed per se for any actions taken internally to specifically operate the apparatus.

Thus, the feedback information may be transferred either by a separate communication system including receivers and transmitters or may be integrated in the energy system, or by means of the communication between the first and the second part of the system. In accordance with one embodiment of the present invention, such an integrated information feedback and energy system comprises an implantable internal energy receiver for receiving wireless energy, the energy receiver having an internal first coil and a first electronic circuit connected to the first coil, and an external energy transmitter for transmitting wireless energy, the energy transmitter having an external second coil and a second electronic circuit connected to the second coil.

The external second coil of the energy transmitter transmits wireless energy which is received by the first coil of the energy receiver. This embodiment of the inventive system further comprises a power switch for switching the connection of the internal first coil to the first electronic circuit on and off, such that feedback information related to the charging of the first coil is received by the external energy transmitter in the form of an impedance variation in the load of the external second coil, when the power switch switches the connection of the internal first coil to the first electronic circuit on and off. In implementing this embodiment of the system, the switch is either separate and controlled by the internal control unit 315, or integrated in the internal control unit 315. It should be understood that the switch 326 should be interpreted in its broadest embodiment. This means a transistor, MCU, MCPU, ASIC FPGA or a DA converter or any other electronic component or circuit that may switch the power on and off.

To conclude, this embodiment of the energy supply arrangement may operate basically in the following manner: The energy balance is first determined by the internal control unit 315 of the determination device. A control signal reflecting the required amount of energy is also created by the internal control unit 315, and the control signal is transmitted from the internal signal transmitter 327 to the external signal receiver 304c. Alternatively, the energy balance can be determined by the external control unit 304b instead depending on the implementation, as mentioned above. In that case, the control signal may carry measurement results from various sensors.

The amount of energy emitted from the external energy source 304a can then be regulated by the external control unit 304b, based on the determined energy balance, e.g. in response to the received control signal. This process may be repeated intermittently at certain intervals during ongoing energy transfer, or may be executed on a more or less continuous basis during the energy transfer.

The amount of transferred energy can generally be regulated by adjusting various transmission parameters in the external energy source 304a, such as voltage, current, amplitude, wave frequency and pulse characteristics.

This system may also be used to obtain information about the coupling factors between the coils in a TET system even to calibrate the system both to find an optimal place for the external coil in relation to the internal coil and to optimize energy transfer. Simply comparing in this case the amount of energy transferred with the amount of energy received. For example if the external coil is moved the coupling factor may vary and correctly displayed movements could cause the external coil to find the optimal place for energy transfer. Preferably, the external coil is adapted to calibrate the amount of transferred energy to achieve the feedback information in the determination device, before the coupling factor is maximized.

This coupling factor information may also be used as a feedback during energy transfer. In such a case, the energy system of the present invention comprises an implantable internal energy receiver for receiving wireless energy, the energy receiver having an internal first coil and a first electronic circuit connected to the first coil, and an external energy transmitter for transmitting wireless energy, the energy transmitter having an external second coil and a second electronic circuit connected to the second coil.

The external second coil of the energy transmitter transmits wireless energy which is received by the first coil of the energy receiver. This system further comprises a feedback device for communicating out the amount of energy received in the first coil as a feedback information, and wherein the second electronic circuit includes a determination device for receiving the feedback information and for comparing the amount of transferred energy by the second coil with the feedback information related to the amount of energy received in the first coil to obtain the coupling factor between the first and second coils. The energy transmitter may regulate the transmitted energy in response to the obtained coupling factor.

Figure 24:
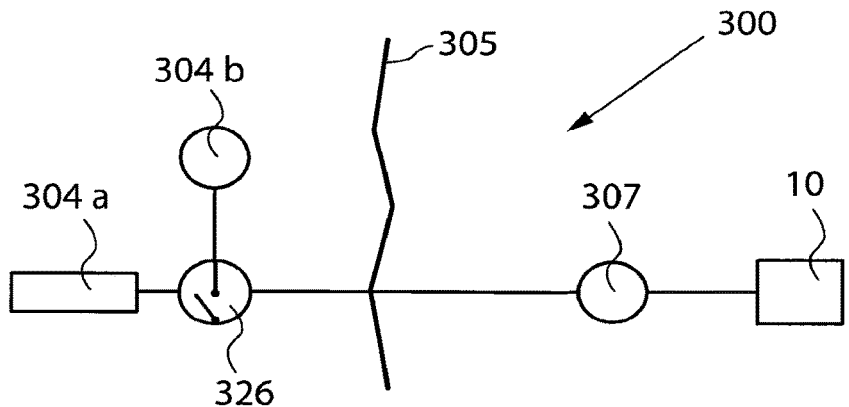
Figure 25:
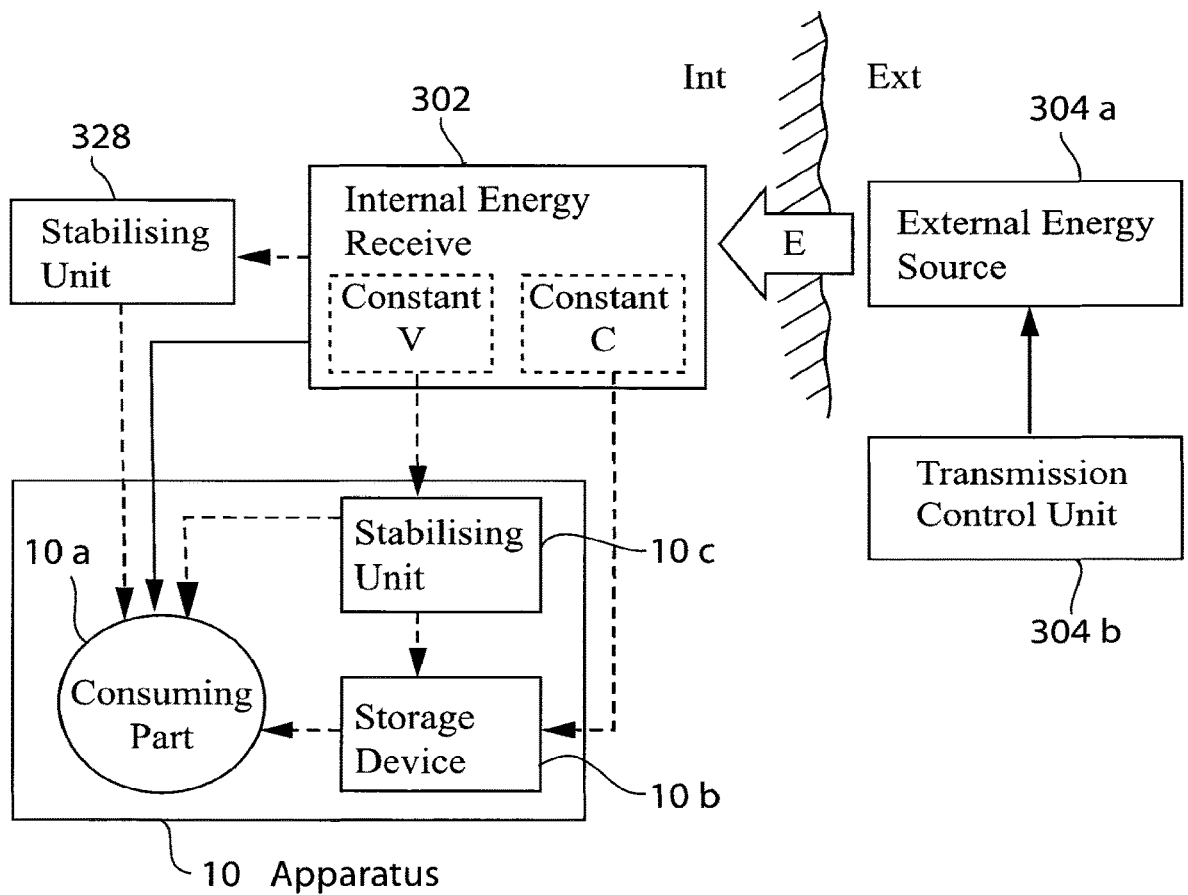

With reference to FIG. 24, although wireless transfer of energy for operating the apparatus has been described above to enable non-invasive operation, it will be appreciated that the apparatus can be operated with wire bound energy as well. Such an example is shown in FIG. 25, wherein an external switch 326 is interconnected between the external energy source 304a and an operation device, such as an electric motor 307 operating the apparatus 10. An external control unit 304b controls the operation of the external switch 326 to effect proper operation of the apparatus 10.

FIG. 25 illustrates different embodiments for how received energy can be supplied to and used by the apparatus 10. Similar to the example of FIG. 24, an internal energy receiver 302 receives wireless energy E from an external energy source 304a which is controlled by a transmission control unit 304b. The internal energy receiver 302 may comprise a constant voltage circuit, indicated as a dashed box "constant V" in the figure, for supplying energy at constant voltage to the apparatus 10. The internal energy receiver 302 may further comprise a constant current circuit, indicated as a dashed box "constant C" in the figure, for supplying energy at constant current to the apparatus 10.

The apparatus 10 comprises an energy consuming part 10a, that requires energy for its electrical operation. The apparatus 10 may further comprise an energy storage device 10b for storing energy supplied from the internal energy receiver 302. Thus, the supplied energy may be directly consumed by the energy consuming part 10a, or stored by the energy storage device 10b, or the supplied energy may be partly consumed and partly stored. The apparatus 10 may further comprise an energy stabilizing unit 10c for stabilizing the energy supplied from the internal energy receiver 302. Thus, the energy may be supplied in a fluctuating manner such that it may be necessary to stabilize the energy before consumed or stored.

The energy supplied from the internal energy receiver 302 may further be accumulated and/or stabilized by a separate energy stabilizing unit 328 located outside the apparatus 10, before being consumed and/or stored by the apparatus 10. Alternatively, the energy stabilizing unit 328 may be integrated in the internal energy receiver 302. In either case, the energy stabilizing unit 328 may comprise a constant voltage circuit and/or a constant current circuit.

It should be noted that FIG. 24 and FIG. 25 illustrate some possible but non-limiting implementation options regarding how the various shown functional components and elements can be arranged and connected to each other. However, the skilled person will readily appreciate that many variations and modifications can be made within the scope of the present invention.

Figure 26:
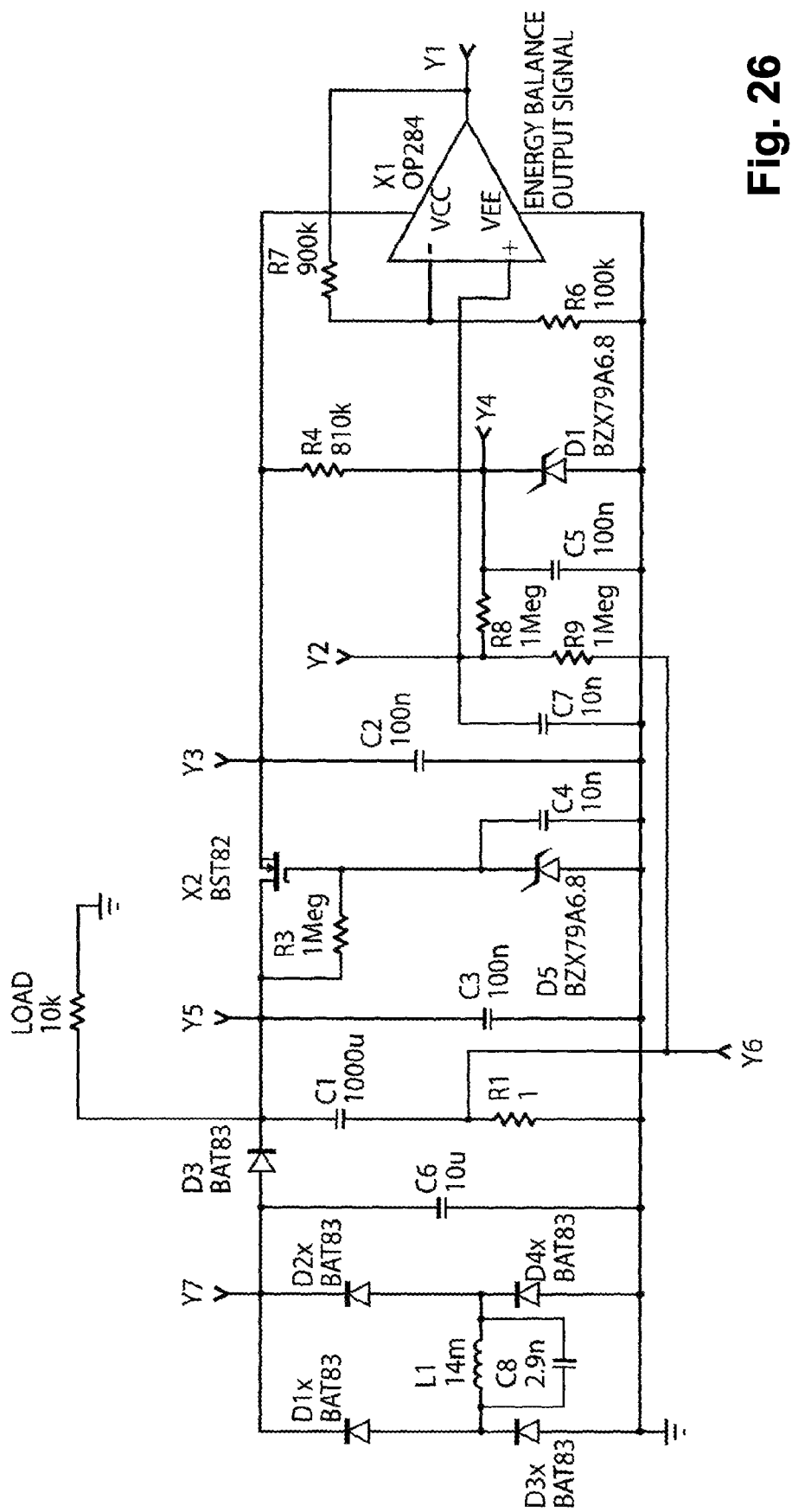

FIG. 26 schematically shows an energy balance measuring circuit of one of the proposed designs of the system for controlling transmission of wireless energy, or energy balance control system. The circuit has an output signal centered on 2.5V and proportionally related to the energy imbalance. The derivative of this signal shows if the value goes up and down and how fast such a change takes place. If the amount of received energy is lower than the energy used by implanted components of the apparatus, more energy is transferred and thus charged into the energy source.

The output signal from the circuit is typically feed to an ND converter and converted into a digital format. The digital information can then be sent to the external energy-transmission device allowing it to adjust the level of the transmitted energy. Another possibility is to have a completely analog system that uses comparators comparing the energy balance level with certain maximum and minimum thresholds sending information to external energy-transmission device if the balance drifts out of the max/min window.

The schematic FIG. 26 shows a circuit implementation for a system that transfers energy to the implanted energy components of the apparatus of the present invention from outside of the patient's body using inductive energy transfer. An inductive energy transfer system typically uses an external transmitting coil and an internal receiving coil.

The implementation of the general concept of energy balance and the way the information is transmitted to the external energy transmitter can of course be implemented in numerous different ways. The schematic FIG. 26 and the above described method of evaluating and transmitting the information should only be regarded as examples of how to implement the control system.

Circuit Details

In FIG. 26 the symbols Y1, Y2, Y3 and so on symbolize test points within the circuit. The components in the diagram and their respective values are values that work in this particular implementation which of course is only one of an infinite number of possible design solutions.

Energy to power the circuit is received by the energy receiving coil L1. Energy to implanted components is transmitted in this particular case at a frequency of 25 kHz. The energy balance output signal is present at test point Y1.

Those skilled in the art will realize that the above various embodiments of the system could be combined in many different ways. For example, an electric switch could be incorporated in any of the embodiments of FIGS. 14-25. Please observe that the switch simply could mean any electronic circuit or component.

The embodiments described in connection with FIGS. 25 and 26 identify a method and a system for controlling transmission of wireless energy to implanted energy consuming components of an electrically operable apparatus. Such a method and system will be defined in general terms in the following.

A method is thus provided for controlling transmission of wireless energy supplied to implanted energy consuming components of an apparatus as described above. The wireless energy E is transmitted from an external energy source located outside the patient and is received by an internal energy receiver located inside the patient, the internal energy receiver being connected to the implanted energy consuming components of the apparatus for directly or indirectly supplying received energy thereto. An energy balance is determined between the energy received by the internal energy receiver and the energy used for the apparatus. The transmission of wireless energy E from the external energy source is then controlled based on the determined energy balance.

The wireless energy may be transmitted inductively from a primary coil in the external energy source to a secondary coil in the internal energy receiver. A change in the energy balance may be detected to control the transmission of wireless energy based on the detected energy balance change. A difference may also be detected between energy received by the internal energy receiver and energy used for the medical device, to control the transmission of wireless energy based on the detected energy difference.

When controlling the energy transmission, the amount of transmitted wireless energy may be decreased if the detected energy balance change implies that the energy balance is increasing, or vice versa. The decrease/increase of energy transmission may further correspond to a detected change rate.

The amount of transmitted wireless energy may further be decreased if the detected energy difference implies that the received energy is greater than the used energy, or vice versa. The decrease/increase of energy transmission may then correspond to the magnitude of the detected energy difference.

As mentioned above, the energy used for the medical device may be consumed to operate the medical device, and/or stored in at least one energy storage device of the medical device.

When electrical and/or physical parameters of the medical device and/or physical parameters of the patient are determined, the energy may be transmitted for consumption and storage according to a transmission rate per time unit which is determined based on said parameters. The total amount of transmitted energy may also be determined based on said parameters.

When a difference is detected between the total amount of energy received by the internal energy receiver and the total amount of consumed and/or stored energy, and the detected difference is related to the integral over time of at least one measured electrical parameter related to said energy balance, the integral may be determined for a monitored voltage and/or current related to the energy balance.

When the derivative is determined over time of a measured electrical parameter related to the amount of consumed and/or stored energy, the derivative may be determined for a monitored voltage and/or current related to the energy balance.

The transmission of wireless energy from the external energy source may be controlled by applying to the external energy source electrical pulses from a first electric circuit to transmit the wireless energy, the electrical pulses having leading and trailing edges, varying the lengths of first time intervals between successive leading and trailing edges of the electrical pulses and/or the lengths of second time intervals between successive trailing and leading edges of the electrical pulses, and transmitting wireless energy, the transmitted energy generated from the electrical pulses having a varied power, the varying of the power depending on the lengths of the first and/or second time intervals.

In that case, the frequency of the electrical pulses may be substantially constant when varying the first and/or second time intervals. When applying electrical pulses, the electrical pulses may remain unchanged, except for varying the first and/or second time intervals. The amplitude of the electrical pulses may be substantially constant when varying the first and/or second time intervals. Further, the electrical pulses may be varied by only varying the lengths of first time intervals between successive leading and trailing edges of the electrical pulses.

A train of two or more electrical pulses may be supplied in a row, wherein when applying the train of pulses, the train having a first electrical pulse at the start of the pulse train and having a second electrical pulse at the end of the pulse train, two or more pulse trains may be supplied in a row, wherein the lengths of the second time intervals between successive trailing edge of the second electrical pulse in a first pulse train and leading edge of the first electrical pulse of a second pulse train are varied.

When applying the electrical pulses, the electrical pulses may have a substantially constant current and a substantially constant voltage. The electrical pulses may also have a substantially constant current and a substantially constant voltage. Further, the electrical pulses may also have a substantially constant frequency. The electrical pulses within a pulse train may likewise have a substantially constant frequency.

The circuit formed by the first electric circuit and the external energy source may have a first characteristic time period or first time constant, and when effectively varying the transmitted energy, such frequency time period may be in the range of the first characteristic time period or time constant or shorter.

A system comprising an apparatus as described above is thus also provided for controlling transmission of wireless energy supplied to implanted energy consuming components of the apparatus. In its broadest sense, the system comprises a control device for controlling the transmission of wireless energy from an energy-transmission device, and an implantable internal energy receiver for receiving the transmitted wireless energy, the internal energy receiver being connected to implantable energy consuming components of the apparatus for directly or indirectly supplying received energy thereto.

The system further comprises a determination device adapted to determine an energy balance between the energy received by the internal energy receiver and the energy used for the implantable energy consuming components of the apparatus, wherein the control device controls the transmission of wireless energy from the external energy-transmission device, based on the energy balance determined by the determination device.

Further, the system may comprise any of the following:

A primary coil in the external energy source adapted to transmit the wireless energy inductively to a secondary coil in the internal energy receiver.

The determination device is adapted to detect a change in the energy balance, and the control device controls the transmission of wireless energy based on the detected energy balance change The determination device is adapted to detect a difference between energy received by the internal energy receiver and energy used for the implantable energy consuming components of the apparatus, and the control device controls the transmission of wireless energy based on the detected energy difference.

The control device controls the external energy-transmission device to decrease the amount of transmitted wireless energy if the detected energy balance change implies that the energy balance is increasing, or vice versa, wherein the decrease/increase of energy transmission corresponds to a detected change rate.

The control device controls the external energy-transmission device to decrease the amount of transmitted wireless energy if the detected energy difference implies that the received energy is greater than the used energy, or vice versa, wherein the decrease/increase of energy transmission corresponds to the magnitude of said detected energy difference.

The energy used for the apparatus is consumed to operate the apparatus, and/or stored in at least one energy storage device of the apparatus.

Where electrical and/or physical parameters of the apparatus and/or physical parameters of the patient are determined, the energy-transmission device transmits the energy for consumption and storage according to a transmission rate per time unit which is determined by the determination device based on said parameters. The determination device also determines the total amount of transmitted energy based on said parameters.

When a difference is detected between the total amount of energy received by the internal energy receiver and the total amount of consumed and/or stored energy, and the detected difference is related to the integral over time of at least one measured electrical parameter related to the energy balance, the determination device determines the integral for a monitored voltage and/or current related to the energy balance.

When the derivative is determined over time of a measured electrical parameter related to the amount of consumed and/or stored energy, the determination device determines the derivative for a monitored voltage and/or current related to the energy balance.

The energy-transmission device comprises a coil placed externally to the human body, and an electric circuit is provided to power the external coil with electrical pulses to transmit the wireless energy. The electrical pulses have leading and trailing edges, and the electric circuit is adapted to vary first time intervals between successive leading and trailing edges and/or second time intervals between successive trailing and leading edges of the electrical pulses to vary the power of the transmitted wireless energy. As a result, the energy receiver receiving the transmitted wireless energy has a varied power.

The electric circuit is adapted to deliver the electrical pulses to remain unchanged except varying the first and/or second time intervals.

The electric circuit has a time constant and is adapted to vary the first and second time intervals only in the range of the first time constant, so that when the lengths of the first and/or second time intervals are varied, the transmitted power over the coil is varied.

The electric circuit is adapted to deliver the electrical pulses to be varied by only varying the lengths of first time intervals between successive leading and trailing edges of the electrical pulses.

The electric circuit is adapted to supplying a train of two or more electrical pulses in a row, said train having a first electrical pulse at the start of the pulse train and having a second electrical pulse at the end of the pulse train, and the lengths of the second time intervals between successive trailing edge of the second electrical pulse in a first pulse train and leading edge of the first electrical pulse of a second pulse train are varied by the first electronic circuit.

The electric circuit is adapted to provide the electrical pulses as pulses having a substantially constant height and/or amplitude and/or intensity and/or voltage and/or current and/or frequency.

The electric circuit has a time constant, and is adapted to vary the first and second time intervals only in the range of the first time constant, so that when the lengths of the first and/or second time intervals are varied, the transmitted power over the first coil are varied.

The electric circuit is adapted to provide the electrical pulses varying the lengths of the first and/or the second time intervals only within a range that includes the first time constant or that is located relatively close to the first time constant, compared to the magnitude of the first time constant.

While specific embodiments of the invention have been illustrated and described herein, it should be realized that numerous other embodiments may be envisaged and that numerous additional advantages, modifications and changes will readily occur to those skilled in the art without departing from the spirit and scope of the invention. Therefore, the invention in its broader aspects is not limited to the specific details, representative devices and illustrated examples shown and described herein. Accordingly, various modifications may be made without departing from the spirit or scope of the general inventive concept as defined by the appended claims and their equivalents, and numerous other embodiments may be envisaged without departing from the spirit and scope of the invention.

The invention is not limited to the examples of embodiments described above and shown in the drawings, but may be freely varied within the scope of the appended claims.

The invention claimed is:

1. A system for communicating with a medical implant in a body of a user, the system comprising:
an implantable command generator configured to receive a voice command from the user; and
a memory configured to store previously received voice commands;
wherein the implantable command generator is configured to:
reduce noise, generated by the body, from the received voice command to generate a noise-reduced voice command,
compare the noise-reduce voice command with the previously received voice commands stored in the memory, and
transmit a command signal, based on the received voice command, to the medical implant in case the noise-reduced voice command corresponds to any of the previously received voice commands stored in the memory.

2. The system according to claim 1, wherein the implantable command generator is configured to reduce the noise in case said noise is above a predetermined level.

3. The system according to claim 1, wherein the previously received voice commands stored in the memory are noise-reduced voice commands.

4. The system according to claim 1, wherein the command generator is configured to be implanted in a proximity of the medical implant.

5. The system according to claim 1, wherein the command generator is configured to be arranged in the medical implant.

6. The system according to claim 1, wherein the command generator is configured to identify a specific noise source in the body.

7. The system according to claim 6, wherein the command generator is configured to reduce the noise in case the specific noise source is identified.

8. The system according to claim 1, wherein the command generator is configured to reduce the noise only in response to the voice command being detected.

9. The system according to claim 1, wherein the command generator is configured to reduce the noise generated from at least one of the intestines, the respiratory system and the heart of the user.

10. The system according to claim 1, wherein the command generator further comprises a training functionality configured to learn which of a number of voice commands that should be interpreted as corresponding to one of a plurality of predetermined commands.

11. The system according to claim 1, wherein the memory is configured to store a plurality of predetermined commands to be transmitted to the medical implant via the command signal.

12. The system according to claim 11, wherein the memory is configured to receive the predetermined commands from a remote control arranged outside of the body.

13. The system according to claim 12, configured to receive the predetermined commands wirelessly from the remote control.

14. The system according to claim 1, configured to be implanted in the abdomen, thorax or pelvic region of the body.

15. The system according to claim 1, further comprising an implantable switch configured to non-invasively control the operation of the medical implant.

16. The system according to claim 1, further comprising a filter configured to reduce the noise.

17. The system according to claim 16, wherein the filter is configured to filter the received voice command against a background of high-frequency losses and frequency distortion caused by the body.

18. The system according to claim 1, further comprising an internal energy source for powering energy consuming components of the system.

19. The system according to claim 18, further comprising an implantable energy receiver configured to be connected to the energy source and to be supplied with energy from outside the body.

20. The system according to claim 19, wherein the energy receiver is configured to be supplied with wirelessly transmitted energy.

* * * * *